(12) United States Patent
Wentland

(10) Patent No.: US 8,541,586 B2
(45) Date of Patent: Sep. 24, 2013

(54) LARGE SUBSTITUENT, NON-PHENOLIC OPIOIDS AND METHODS OF USE THEREOF

(75) Inventor: Mark P. Wentland, Watervliet, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 74 days.

(21) Appl. No.: 13/215,392

(22) Filed: Aug. 23, 2011

(65) Prior Publication Data
US 2011/0306603 A1 Dec. 15, 2011

Related U.S. Application Data

(63) Continuation of application No. 12/477,223, filed on Jun. 3, 2009, now Pat. No. 8,026,252, which is a continuation of application No. 11/459,203, filed on Jul. 21, 2006, now Pat. No. 7,557,119.

(60) Provisional application No. 60/701,407, filed on Jul. 21, 2005.

(51) Int. Cl.
C07D 211/08 (2006.01)
C07D 211/06 (2006.01)

(52) U.S. Cl.
USPC .......................................... 546/234; 546/233

(58) Field of Classification Search
USPC .................... 514/331; 546/233, 234
See application file for complete search history.

(56) References Cited

U.S. PATENT DOCUMENTS 6,812,236 B2 * 11/2004 Gibson et al. ................. 514/317

FOREIGN PATENT DOCUMENTS

| WO | 2004013120 A1 | 2/2004 |
|----|---------------|--------|
| WO | 2005042491 A1 | 5/2005 |
| WO | 2006069276 A2 | 6/2006 |
| WO | 2006138528 A2 | 12/2006 |
| WO | 2007030089 A1 | 3/2007 |

OTHER PUBLICATIONS

Black SL, et al. The Role of the Side Chain in Determining Relative d- and k-Affinity in C5'-Substituted Analogues of Naltrindole, J. Med. Chem. 46:314-317. 2003.

* cited by examiner

*Primary Examiner* — Charanjit Aulakh
(74) *Attorney, Agent, or Firm* — Heslin Rothenberg Farley & Mesiti PC

(57) ABSTRACT

8-Substituted-2,6-methano-3-benzazocines of general structure

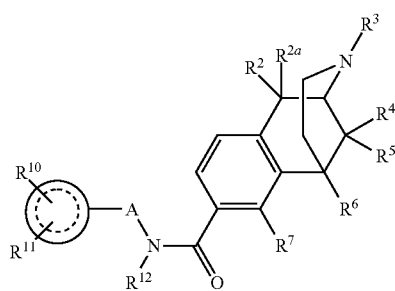

are useful as analgesics, anti-diarrheal agents, anticonvulsants, antitussives and anti-addiction medications.

1 Claim, No Drawings

LARGE SUBSTITUENT, NON-PHENOLIC OPIOIDS AND METHODS OF USE THEREOF

CROSS REFERENCE TO RELATED APPLICATIONS

This application is a continuation of allowed U.S. application Ser. No. 12/477,223, filed Jun. 3, 2009, which is a continuation of U.S. application Ser. No. 11/459,203, filed Jul. 21, 2006, and issued as U.S. Pat. No. 7,557,119 on Jul. 7, 2009, and claims priority of U.S. provisional application 60/701,407, filed Jul. 21, 2005, the entire disclosures of which are incorporated herein by reference.

FEDERALLY SPONSORED RESEARCH

The following invention was made with Government support under contract number 5 R01 DA12180 awarded by U.S. Dept of Health and Human Services. The Government has certain rights in this invention.

FIELD OF THE INVENTION

The invention relates to opioid receptor binding compounds containing carboxamides that have large substitutents on the nitrogen of the carboxamide. The compounds are useful as analgesics, anti-diarrheal agents, anticonvulsants, anti-obesity agents, antitussives, anti-cocaine, and anti-addiction medications.

BACKGROUND OF THE INVENTION

Opiates have been the subject of intense research since the isolation of morphine in 1805, and thousands of compounds having opiate or opiate-like activity have been identified. Many opioid receptor-interactive compounds including those used for producing analgesia (e.g., morphine) and those used for treating drug addiction (e.g., naltrexone and cyclazocine) in humans have limited utility due to poor oral bioavailability and a very rapid clearance rate from the body. This has been shown in many instances to be due to the presence of the 8-hydroxyl group (OH) of 2,6-methano-3-benzazocines, also known as benzomorphans [(e.g., cyclazocine and EKC (ethylketocyclazocine)] and the corresponding 3-OH group in morphinanes (e.g., morphine).

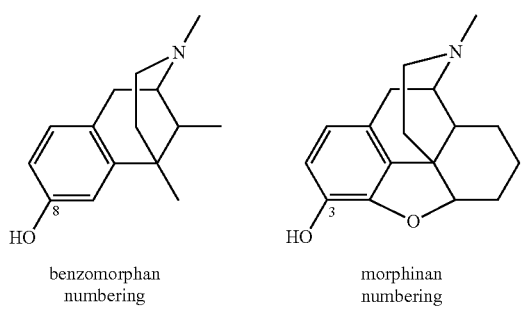 [SMILES: CC1C2Cc3ccc(O)cc3C1(C)CCN2C ; CN1CCC23c4c5ccc(O)c4OC2CCCC3C1C5]

The high polarity of these hydroxyl groups retards oral absorption of the parent molecules. Furthermore, the 8-(or 3-)OH group is prone to sulfonation and glucuronidation (Phase II metabolism), both of which facilitate rapid excretion of the active compounds, leading to disadvantageously short half-lives for the active compounds. Until the publications of Wentland in 2001, the uniform experience in the art of the past seventy years had been that removal or replacement of the 8-(or 3-) OH group had led to pharmacologically inactive compounds.

U.S. Pat. No. 6,784,187 (to Wentland) disclosed that the phenolic OH of opioids could be replaced by CONH2. In the cyclazocine series of opioids, it was shown that 8-carboxamidocyclazocine (8-CAC) had high affinity for μ and κ opioid receptors. In studies in vivo, 8-CAC showed high antinociception activity and a much longer duration of action than cyclazocine (15 h vs. 2 h) when both were dosed at 1 mg/kg ip in mice. Preliminary structure-activity relationship studies for 8-CAC revealed that mono-substitution of the carboxamide nitrogen with methyl or phenyl reduced binding affinity for guinea pig μ receptors 75- and 2313-fold, respectively whereas dimethylation of the carboxamide group reduced binding affinity 9375-fold. The finding that substitution of the carboxamide nitrogen had such a detrimental effect suggested that the NH2 of the amide was critical to opioid binding.

SUMMARY OF THE INVENTION

We have now found that the nitrogen of the carboxamide can be substituted with fairly large and relatively non-polar groups, and that such compounds exhibit excellent opioid binding and, presumably, good metabolic stability. The compounds of the invention are therefore useful as analgesics, anti-pruritics, anti-diarrheal agents, anticonvulsants, antitussives, anorexics and as treatments for hyperalgesia, drug addiction, respiratory depression, dyskinesia, pain (including neuropathic pain), irritable bowel syndrome and gastrointestinal motility disorders. Drug addiction, as used herein, includes alcohol and nicotine addiction. There is evidence in the literature that the compounds may also be useful as immunosuppressants and antiinflammatories and for reducing ischemic damage (and cardioprotection), for improving learning and memory, and for treating urinary incontinence.

In one aspect, the invention relates to compounds of formula:

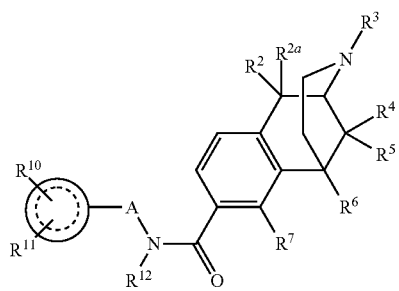

wherein

is an aryl or heteroaryl residue of one to three rings;

A is $(CH_2)_n$, wherein one or more $CH_2$ may be replaced by —O—, cycloalkyl or —$CR^{1a}R^{1b}$—;

$R^{1a}$ and $R^{1b}$ are chosen independently from hydrogen, halogen, lower alkyl, lower alkoxy and lower alkylthio;

$R^2$ and $R^{2a}$ are both hydrogen or taken together $R^2$ and $R^{2a}$ are =O;

$R^3$ is chosen from hydrogen, $C_1$-$C_8$ hydrocarbon, heterocyclyl, heterocyclylalkyl and hydroxyalkyl;

$R^4$ is chosen from hydrogen, hydroxy, amino, lower alkoxy, $C_1$-$C_{20}$ alkyl and $C_1$-$C_{20}$ alkyl substituted with hydroxy or carbonyl;

$R^5$ is lower alkyl;

$R^6$ is lower alkyl;

$R^7$ is chosen from hydrogen and hydroxy; or together $R^4$, $R^5$, $R^6$ and $R^7$ may form from one to three rings, said rings having optional additional substitution;

$R^{10}$ is one or two residues chosen independently from hydrogen, hydroxyl, halogen, $(C_1$-$C_6)$alkyl, $(C_1$-$C_6)$alkoxy, halo$(C_1$-$C_6)$alkyl and halo$(C_1$-$C_6)$alkoxy and $(C_1$-$C_6)$alkylthio;

$R^{11}$ is H or

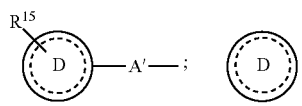

is an aryl or heteroaryl residue of one to three rings;

A' is $(CH_2)_m$, wherein one or more $CH_2$ may be replaced by —O—, cycloalkyl, —$CR^{1a}R^{1b}$, —C(=O)— or —NH—;

$R^{12}$ is chosen from hydrogen and lower alkyl;

$R^{15}$ is one or two residues chosen independently from hydrogen, hydroxyl, halogen, $(C_1$-$C_6)$alkyl, $(C_1$-$C_6)$alkoxy, halo$(C_1$-$C_6)$alkyl and halo$(C_1$-$C_6)$alkoxy and $(C_1$-$C_6)$alkylthio;

m is zero or an integer from 1 to 6; and n is an integer from 1 to 6.

Subclasses of the foregoing structure include:

II. 2,6-methano-3-benzazocines of the structure shown above, in which $R^4$, $R^5$, $R^6$ and $R^7$ do not form additional rings:

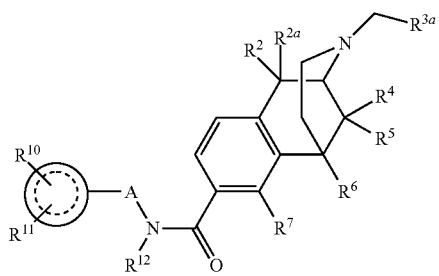

wherein:

$R^{3a}$ is chosen from hydrogen, $C_1$-$C_7$ hydrocarbon, heterocyclyl, and hydroxyalkyl;

$R^4$ is chosen from hydrogen, hydroxy, lower alkoxy, $C_1$-$C_{20}$ alkyl and $C_1$-$C_{20}$ alkyl substituted with hydroxy or carbonyl;

$R^5$ is lower alkyl;

$R^6$ is lower alkyl; and $R^7$ is hydrogen or hydroxy.

III. morphinans in which $R^5$ and $R^6$ form one ring:

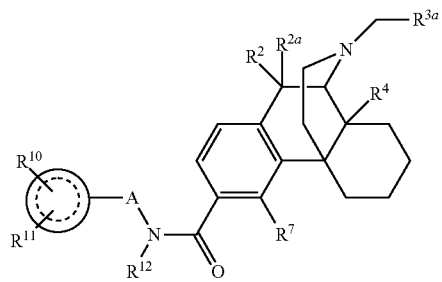

wherein $R^{3a}$ is chosen from hydrogen, $C_1$-$C_7$ hydrocarbon, heterocyclyl, and hydroxyalkyl; and $R^7$ is H or OH.

IV. morphinans in which $R^5$, $R^6$ and $R^7$ form two rings:

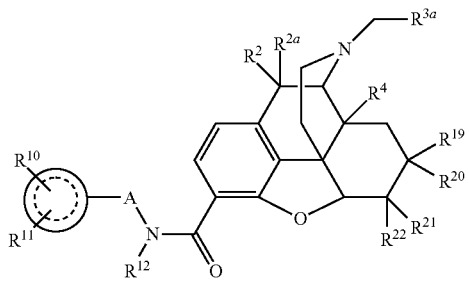

wherein $R^{19}$ is hydrogen or lower alkyl;

$R^{20}$ is chosen from hydrogen, lower alkyl and hydroxy (lower alkyl); or together, $R^9$ and $R^{10}$ form a spiro-fused carbocycle of 5 to 10 carbons;

$R^{21}$ is hydrogen;

$R^{22}$ is chosen from hydroxy, lower alkoxy and —$NR^{13}R^{14}$; or together, $R^{21}$ and $R^{22}$ form a carbonyl or a vinyl substituent. and V. morphinans wherein $R^4$ and $R^{11}$ form an additional sixth ring, which may be saturated or unsaturated:

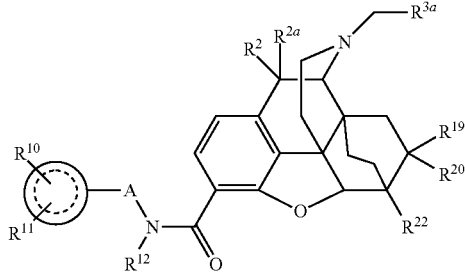

or

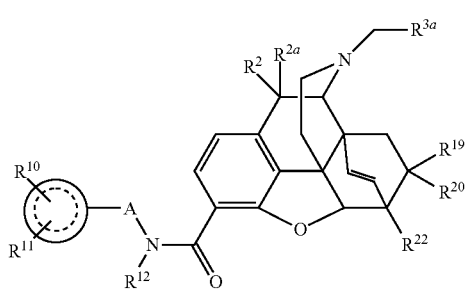

In another aspect, the invention relates to a method for preparing a second compound that interacts with an opioid receptor when a first compound that interacts with an opioid receptor is known. When the first compound contains a phenolic hydroxyl, the method comprises converting the phenolic hydroxyl to a residue of structure:

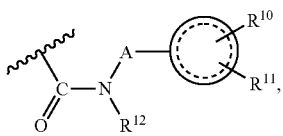

which will hereinafter be sometimes referred to as Q.

In another aspect, the invention relates to methods for inhibiting, eliciting or enhancing responses mediated by an opioid receptor comprising:
  (a) providing a first compound that inhibits, elicits or enhances an opioid receptor response;
  (b) preparing a second compound that interacts with an opioid receptor by converting a phenolic hydroxyl group on the first compound to a residue described as Q above; and
  (c) bringing the second compound into contact with the opioid receptor.

In another aspect, the invention relates to a method for treating a disease by altering a response mediated by an opioid receptor. The method comprises bringing into contact with the opioid receptor a compound having the formula

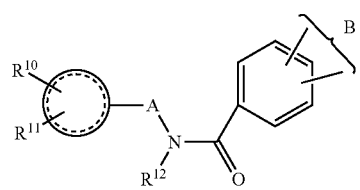

wherein
B represents the appropriate residue of a known compound of formula

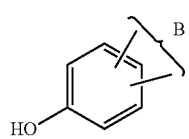

and the known compound of that formula alters a response mediated by an opioid receptor.

DETAILED DESCRIPTION OF THE INVENTION

From many years of SAR studies, it is known that the hydroxyl of morphinans and benzomorphans interacts with a specific site in the opiate receptor. We have now surprisingly found that the hydroxyl can be replaced with a very large carboxamide residue. A fairly wide range of secondary carboxamides exhibit binding in the desired range below 25 nanomolar.

Since phenolic hydroxyls of benzomorphans and morphinans can be chemically converted to carboxamides by a simple, flexible and convenient route described in U.S. Pat. Nos. 6,784,187 and 7,057,035, the door is opened to a whole family of new therapeutic agents, many of which derive directly from the application of the principles set forth herein to known therapeutic agents that rely on opioid binding for their activity. Moreover, since the receptor seems to tolerate some variation in Q, one may contemplate further modulating receptor specificity, affinity and tissue distribution by varying the properties of the aryl substituents.

In one aspect the invention relates to compounds of formula

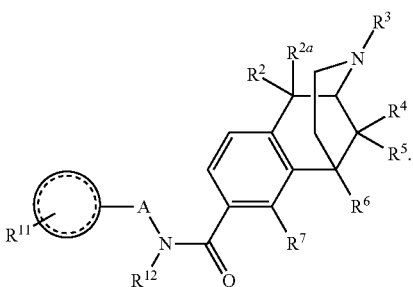

In one major subclass, $R^{11}$ is

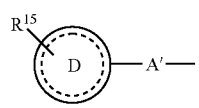

and the compounds are biphenyls, diaryl ethers and the like of formula:

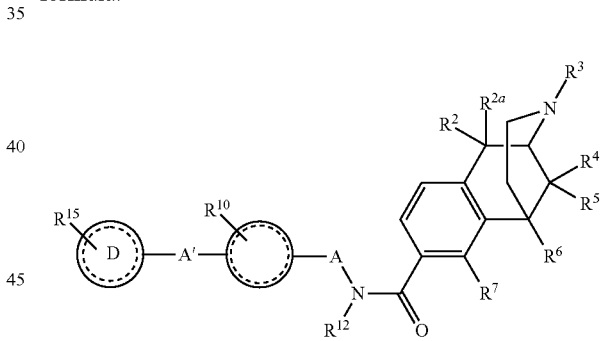

Preferred values of Q

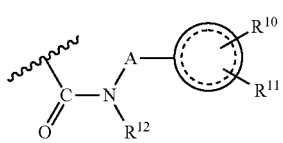

are those in which
  (a)

is phenyl, $R^{10}$ is hydrogen and $R^{11}$ is

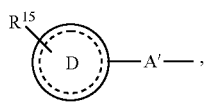

so that $R^{11}$ represents pyridinyl, phenyl, halophenyl, methylphenyl, methoxyphenyl (in all of which A' is a direct bond) and phenoxy (in which A' is —O—).

(b)

is chosen from phenyl, naphthyl, fluorenyl, carbazole, dibenzofuran and dibenzothiophene, $R^{10}$ is hydrogen, methoxy, halogen or methyl; and $R^{11}$ is hydrogen;

(c)

is pyridinyl, $R^{10}$ is hydrogen and $R^{11}$ is chosen from phenyl, halophenyl, methylphenyl, methoxyphenyl and phenoxy.

It is known in the art that compounds that are μ, δ and κ agonists exhibit analgesic activity; compounds that are selective μ agonists exhibit anti-diarrheal activity and are useful in treating dyskinesia; μ antagonists and κ agonists are useful in treating heroin, cocaine, alcohol and nicotine addiction; κ agonists are also anti-pruritic agents and are useful in treating hyperalgesia. Recently it has been found [Peterson et al. *Biochem. Pharmacol.* 61, 1141-1151 (2001)] that κ agonists are also useful in treating retroviral inflections. In general, the dextrorotatory isomers of morphinans of type III above are useful as antitussives and anticonvulsants.

Opioid receptor ligands having known high affinity are shown in the following charts. Replacement of OH with Q in these compounds produces compounds that exhibit similar activity and better bioavailability.

Chart 1. Opioid Receptor Ligands Benzomorphinans (a.k.a. 2,6-Methano-3-benzazocines)

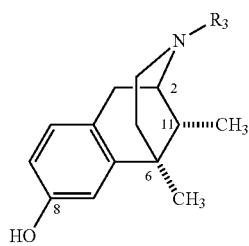

Cyclazocine, $R_3 = CH_2$-c-$C_3H_5$
Metazocine, $R_3 = CH_3$
Phenazocine, $R_3 = CH_2C_6H_5$
SKF 10,047, $R_3 = CH_2CH=CH_2$
Pentazocine, $R_3 = CH_2CH=C(CH_3)_2$
(all racemic)

-continued

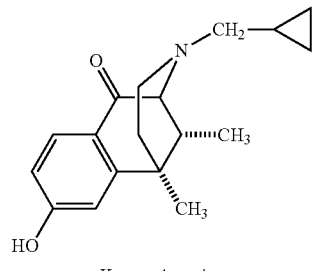

Ketocyclazocine

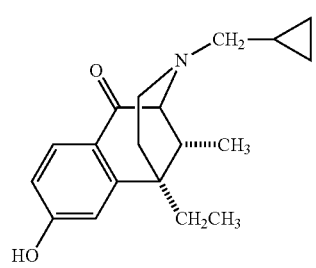

Ethylketocyclazocine (EKC)

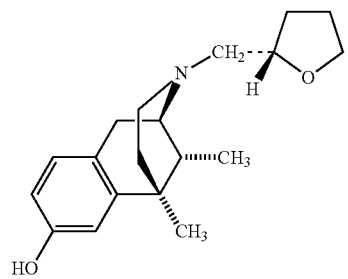

MR2034-"Merz" core structure (opt. active)

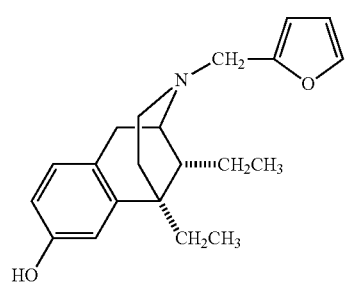

MR2266

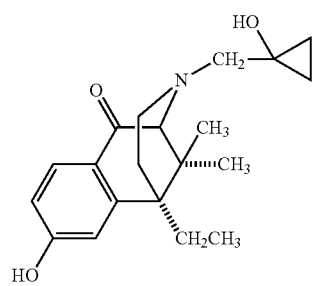

Bremazocine

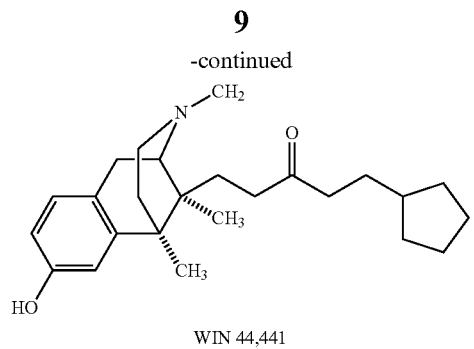
WIN 44,441
Chart 2. Opioid Receptor Ligands Morphine and Morphinans
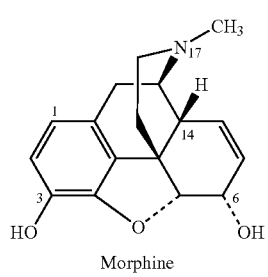
Morphine
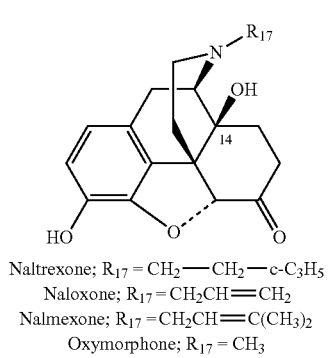
Naltrexone; $R_{17} = CH_2-CH_2-c-C_3H_5$
Naloxone; $R_{17} = CH_2CH=CH_2$
Nalmexone; $R_{17} = CH_2CH=C(CH_3)_2$
Oxymorphone; $R_{17} = CH_3$
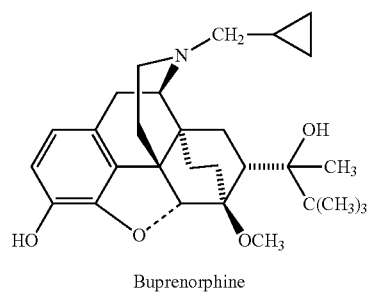
Buprenorphine
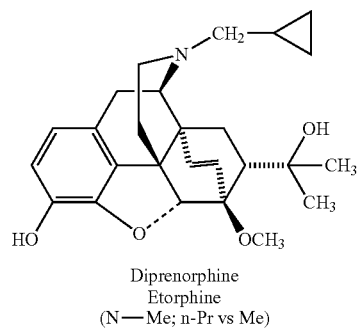
Diprenorphine
Etorphine
(N—Me; n-Pr vs Me)
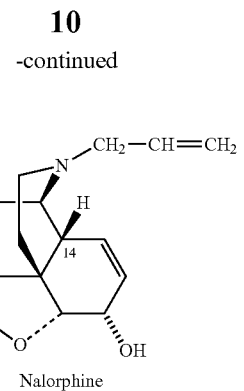
Nalorphine
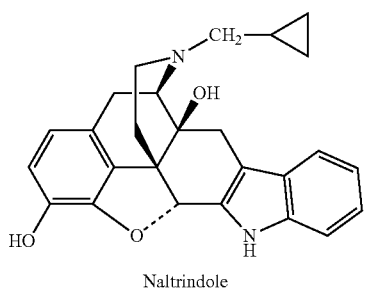
Naltrindole
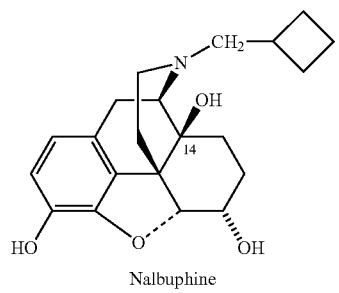
Nalbuphine
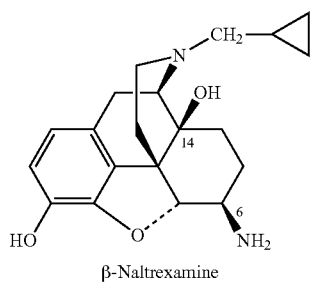
β-Naltrexamine
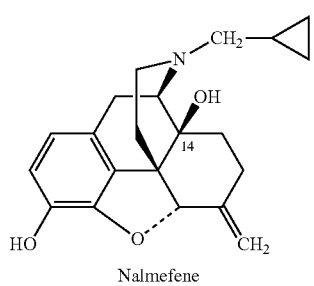
Nalmefene

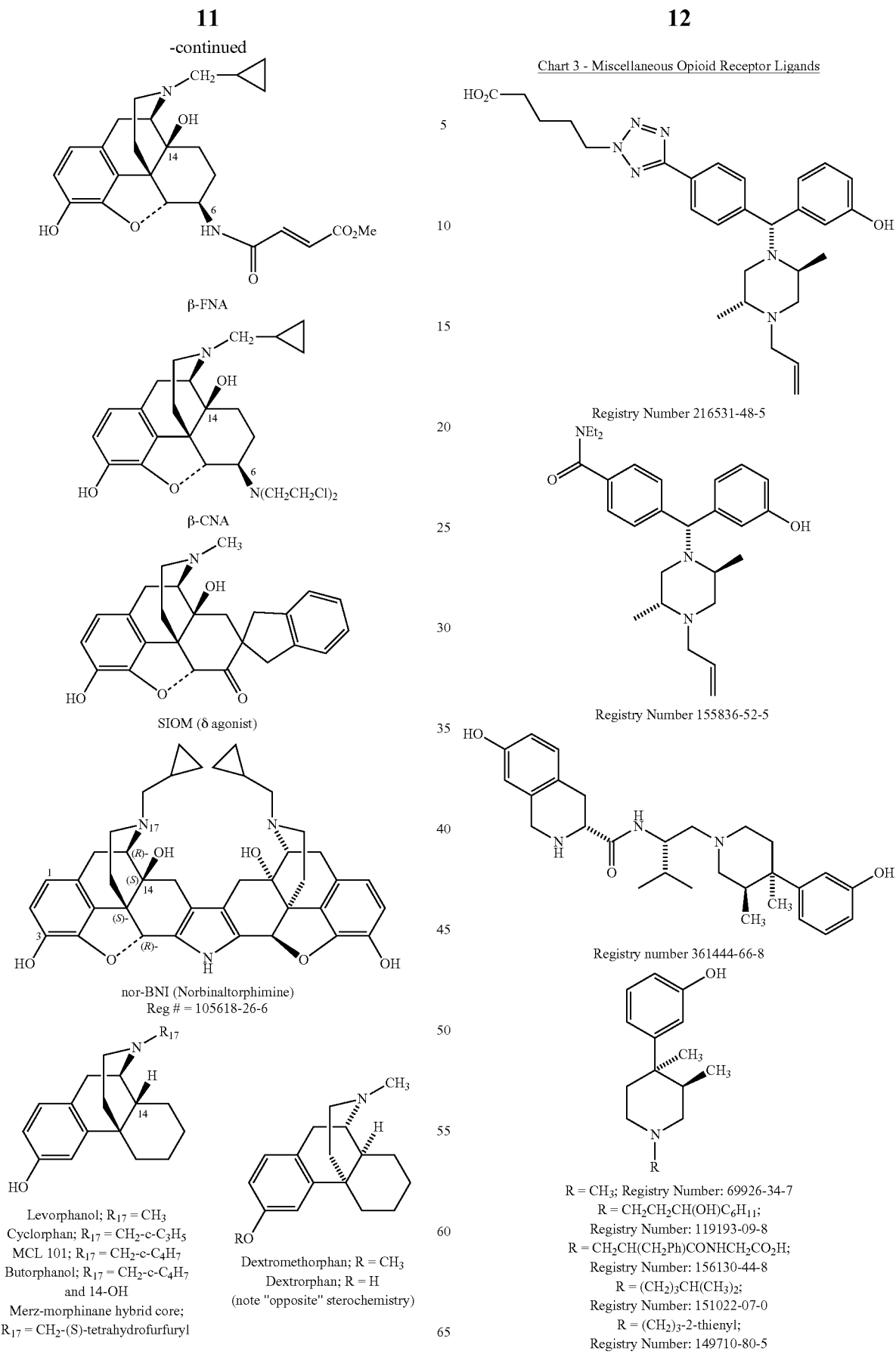

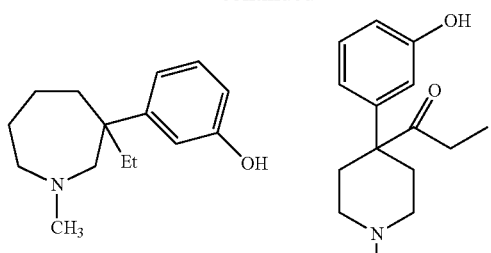

Meptazinol
Registry Number 59263-76-2

Ketobemidone
Registry Number 469-79-4

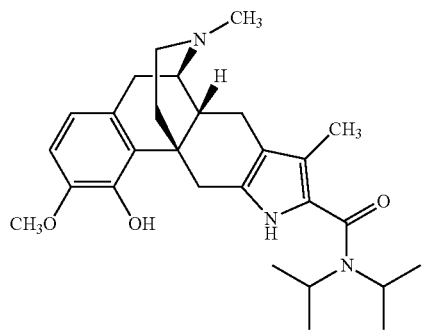

Registry Number 177284-71-8

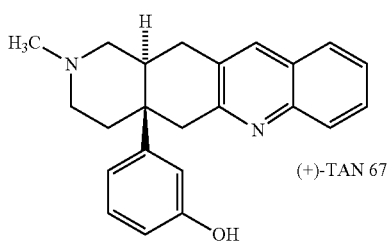

(+)-TAN 67

Registry Number 189263-70-5

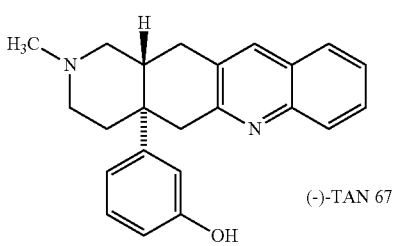

(-)-TAN 67

Registry Number 173398-79-3

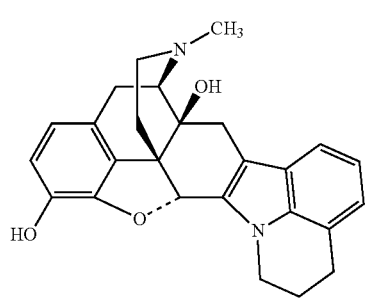

Registry Number 189016-07-7

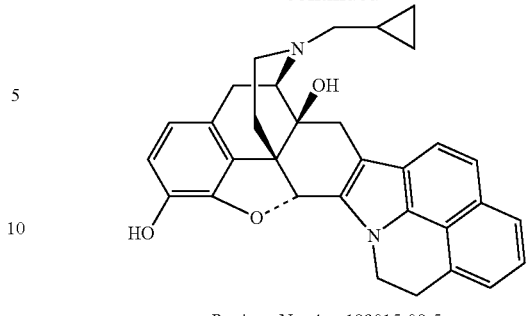

Registry Number 189015-08-5

Other opioid receptor ligands are described in Aldrich, J. V. "Analgesics" in *Burger's Medicinal Chemistry and Drug Discovery*, M. E. Wolff ed., John Wiley & Sons 1996, pages 321-44, the disclosures of which are incorporated herein by reference. In all but two of the foregoing compounds, there is a single phenolic OH that is to be replaced by Q according to the present invention. In norbinaltorphimine and 361444-66-8, there are two phenolic OH's, either or both of which are replaced by Q.

We have examined the opioid receptor binding of a series of analogs of known compounds that interact at opioid receptors in which the OH is replaced by the Q-group shown in Tables 1-3. Binding assays used to screen compounds are similar to those previously reported by Neumeyer et al., Design and Synthesis of Novel Dimeric Morphinan Ligands for κ and μ Opioid Receptors. *J. Med. Chem.* 2003, 46, 5162. Membrane protein from CHO cells that stably expressed one type of the human opioid receptor were incubated with 12 different concentrations of the compound in the presence of either 1 nM [$^3$H]U69,593[10] (κ), 0.25 nM [$^3$H]DAMGO[11] (μ) or 0.2 nM [$^3$H]naltrindole[12] (δ) in a final volume of 1 mL of 50 mM Tris-HCl, pH 7.5 at 25° C. Incubation times of 60 min were used for [$^3$H]U69,593 and [$^3$H]DAMGO. Because of a slower association of [$^3$H]naltrindole with the receptor, a 3 h incubation was used with this radioligand. Samples incubated with [$^3$H]naltrindole also contained 10 mM $MgCl_2$ and 0.5 mM phenylmethylsulfonyl fluoride. Nonspecific binding was measured by inclusion of 10 μM naloxone. The binding was terminated by filtering the samples through Schleicher & Schuell No. 32 glass fiber filters using a Brandel 48-well cell harvester. The filters were subsequently washed three times with 3 mL of cold 50 mM Tris-HCl, pH 7.5, and were counted in 2 mL Ecoscint A scintillation fluid. For [$^3$H]naltrindole and [$^3$H]U69,593 binding, the filters were soaked in 0.1% polyethylenimine for at least 60 min before use. $IC_{50}$ values were calculated by least squares fit to a logarithm-probit analysis. $K_i$ values of unlabeled compounds were calculated from the equation $K_i=(IC_{50})/1+S$ where S=(concentration of radioligand)/($K_d$ of radioligand).[13] Data are the mean±SEM from at least three experiments performed in triplicate.

[$^{35}$S]GTPγS Binding Assays. In a final volume of 0.5 mL, 12 different concentrations of each test compound were incubated with 15 μg (κ), 10 μg (δ) or 7.5 μg (μ) of CHO cell membranes that stably expressed either the human κ, δ or μ opioid receptor. The assay buffer consisted of 50 mM Tris-HCl, pH 7.4, 3 mM $MgCl_2$, 0.2 mM EGTA, 3 μM GDP, and 100 mM NaCl. The final concentration of [$^{35}$S]GTPγS was 0.080 nM. Nonspecific binding was measured by inclusion of 10 μM GTPγS. Binding was initiated by the addition of the membranes. After an incubation of 60 min at 30° C., the samples were filtered through Schleicher & Schuell No. 32 glass fiber filters. The filters were washed three times with cold 50 mM Tris-HCl, pH 7.5, and were counted in 2 mL of Ecoscint scintillation fluid. Data are the mean $E_{max}$ and $EC_{50}$ values±S.E.M. from at least three separate experiments, performed in triplicate. For calculation of the $E_{max}$ values, the basal [$^{35}$S]GTPγS binding was set at 0%. To determine antagonist activity of a compound at the μ opioid receptors, CHO membranes expressing the μ opioid receptor, were incubated with 12 different concentrations of the compound in the presence of 200 nM of the μ agonist DAMGO. To determine antagonist activity of a compound at the κ opioid receptors, CHO membranes expressing the κ opioid receptor, were incubated with the compound in the presence of 100 nM of the κ agonist U50,488. To determine if a compound was an antagonist at δ receptors, CHO membranes expressing the δ receptor were incubated with 12 different concentrations of the test compound in the presence of 10 nM of the δ-selective agonist SNC 80.

TABLE 1

Cyclazocine subseries $K_i$ (nM ± S.E.)

| Example # | optical isomer | Q | [$^3$H] DAMGO (μ) | [$^3$H] Naltrindole (δ) | [$^3$H] U69,593 (κ) |
|---|---|---|---|---|---|
| 15 | (±)- | CONH(CH$_2$)$_2$(4-C$_6$H$_4$C$_6$H$_5$) | 0.048 ± 0.0014 | 0.94 ± 0.045 | 0.33 ± 0.015 |
| 42 | (±)- | CONH(CH$_2$)$_2$(4-C$_6$H$_4$C$_6$H$_5$) | 0.30 ± 0.036 | 0.74 ± 0.019 | 1.8 ± 0.19 |
| 43 | (±)- | CONH(CH$_2$)$_2$(4-C$_6$H$_4$C$_6$H$_5$) | 0.26 ± 0.006 | 0.70 ± 0.073 | 2.3 ± 0.048 |
| 16 | (−)- | CONH(CH$_2$)$_2$(4-C$_6$H$_4$C$_6$H$_5$) | 0.017 ± 0.004 | 0.32 ± 0.08 | 0.046 ± 0.01 |
| 16 | (−) | CONH(CH$_2$)$_2$(4-C$_6$H$_4$C$_6$H$_5$) | 0.25 ± 0.031 | 0.24 ± 0.014 | 0.35 ± 0.009 |
| 17 | (+) | CONH(CH$_2$)$_2$(4-C$_6$H$_4$C$_6$H$_5$) | 7.8 ± 2.0 | 21 ± 0.74 | 11 ± 1.3 |
| 17 | (+) | CONH(CH$_2$)$_2$(4-C$_6$H$_4$C$_6$H$_5$) | 6.4 ± 0.50 | 9.9 ± 0.44 | 8.5 ± 1.07 |
| 18 | (±)- | CONH(CH$_2$)$_3$(4-C$_6$H$_4$C$_6$H$_5$) | 5.8 ± 0.31 | 72 ± 11 | 2.7 ± 0.21 |
| 19 | (±)- | CON(CH$_3$)(CH$_2$)$_2$(4-C$_6$H$_4$C$_6$H$_5$) | 6.7 ± 1.7 | 12 ± 2.4 | 11 ± 0.44 |
| 44 | (±)- | CONH-c-C$_3$H$_4$—(4-C$_6$H$_4$C$_6$H$_5$)(trans) | 13 ± 0.69 | 20 ± 2.9 | 36 ± 6.8 |
| 45 | (±)- | CONH-c-C$_3$H$_4$—(4-C$_6$H$_4$C$_6$H$_5$)(cis) | 12 ± 2.4 | 20 ± 1.4 | 21 ± 4.8 |
| 46 | (±)- | CONHCH$_2$CH(CH$_3$)(4-C$_6$H$_4$C$_6$H$_5$) | 18 ± 1.1 | 12 ± 0.11 | 15 ± 1.0 |
| 47 | (±)- | CONHCH(CH$_3$)CH$_2$(4-C$_6$H$_4$C$_6$H$_5$) | 7.8 ± 0.99 | 7.6 ± 0.51 | 11 ± 0.24 |
| 48 | (±)- | CONH(CH$_2$)$_2$(4-C$_6$H$_4$—4-CH$_3$OC$_6$H$_4$) | 0.084 ± 0.012 | 0.18 ± 0.022 | 1.5 ± 0.10 |
| 49 | (±)- | CONH(CH$_2$)$_2$(4-C$_6$H$_4$—4-ClC$_6$H$_4$) | 0.20 ± 0.038 | 0.71 ± 0.046 | 3.2 ± 0.67 |
| 50 | (±)- | CONH(CH$_2$)$_2$(4-C$_6$H$_4$—3-ClC$_6$H$_4$) | 0.56 ± 0.087 | 1.3 ± 0.19 | 3.8 ± 0.13 |
| 51 | (±)- | CONH(CH$_2$)$_2$(4-C$_6$H$_4$—4-CH$_3$C$_6$H$_4$) | 0.29 ± 0.075 | 0.72 ± 0.027 | 3.3 ± 0.20 |
| 52 | (±)- | CONH(CH$_2$)$_2$(2-Br—C$_6$H$_4$) | 4.0 ± 0.36 | 150 ± 6.2 | 19 ± 1.3 |
| 30 | (±)- | CONH(CH$_2$)$_2$(3-Br—C$_6$H$_4$) | 0.35 ± 0.021 | 3.5 ± 0.19 | 0.063 ± 0.006 |
| 29 | (±)- | CONH(CH$_2$)$_2$(4-Br—C$_6$H$_4$) | 2.4 ± 0.33 | 2.5 ± 0.28 | 0.38 ± 0.060 |
| 53 | (±)- | CONH(CH$_2$)$_2$(4-C$_6$H$_4$)CONH(CH$_2$)$_2$(4-BrC$_6$H$_4$) | 1.5 ± 0.18 | 30 ± 1.8 | 5.0 ± 0.36 |
| 37 | (±)- | CONH(CH$_2$)$_2$(2-naphthyl) | 0.18 ± 0.009 | 0.90 ± 0.020 | 0.20 ± 0.056 |
| 38 | (±)- | CONH(CH$_2$)$_3$(2-naphthyl) | 1.9 ± 0.19 | 18 ± 1.2 | 0.18 ± 0.016 |
| 40 | (±)- | CONH(CH$_2$)$_2$(1-naphthyl) | 4.2 ± 0.13 | 24 ± 1.2 | 2.4 ± 0.46 |
| 41 | (±)- | CONH(CH$_2$)$_3$(1-naphthyl) | 2.4 ± 0.45 | 18 ± 1.0 | 1.9 ± 0.077 |
| 25 | (±)- | CONH(CH$_2$)$_2$(3-C$_6$H$_4$C$_6$H$_5$) | 0.95 ± 0.15 | 5.9 ± 1.2 | 2.2 ± 0.14 |
| 26 | (±)- | CONH(CH$_2$)$_2$(2-C$_6$H$_4$C$_6$H$_5$) | 6.7 ± 0.49 | 21 ± 3.1 | 2.4 ± 0.28 |
| 33 | (±)- | CONH(CH$_2$)$_2$(4-C$_6$H$_4$—O—C$_6$H$_5$) | 0.059 ± 0.017 | 3.2 ± 0.30 | 1.6 ± 0.30 |
| 35 | (±)- | CONH(CH$_2$)$_2$(3-C$_6$H$_4$—O—C$_6$H$_5$) | 0.63 ± 0.090 | 12 ± 1.9 | 0.85 ± 0.070 |
| 34 | (±)- | CONH(CH$_2$)$_2$(2-C$_6$H$_4$—O—C$_6$H$_5$) | 0.54 ± 0.16 | 95 ± 6.7 | 13 ± 0.67 |
| 54 | (±)- | CONH(CH$_2$)$_2$(4-C$_6$H$_4$-4-pyridinyl) | 0.065 ± 0.0089 | 6.7 ± 0.58 | 1.8 ± 0.12 |
| 55 | (±)- | CONH(CH$_2$)$_2$(4-C$_6$H$_4$-3-pyridinyl) | 0.064 ± 0.0051 | 8.2 ± 0.50 | 2.2 ± 0.043 |
| 56 | (±)- | CONH(CH$_2$)$_2$(4-C$_6$H$_4$-2-pyridinyl) | 0.33 ± 0.032 | 9.2 ± 1.3 | 3.3 ± 0.089 |
| 57 | (±)- | CONH(CH$_2$)$_2$(3-pyridinyl-4-C$_6$H$_5$) | 0.61 ± 0.14 | 14 ± 1.2 | 2.6 ± 0.12 |
| 58 | (±)- | CONH(CH$_2$)$_2$(2-pyridinyl-4-C$_6$H$_5$) | 0.82 ± 0.095 | 6.5 ± 0.81 | 1.4 ± 0.16 |
| 59 |  |  |  |  |  |
| 11 | (±)- | CONH(CH$_2$)$_2$C$_6$H$_5$ | 3.5 ± 0.27 | 59 ± 6.6 | 1.7 ± 0.18 |
| 12 | (±)- | CONH(CH$_2$)$_3$C$_6$H$_5$ | 2.5 ± 0.27 | 47 ± 1.6 | 3.0 ± 0.35 |
| 60 | (±)- | CONH(CH$_2$)$_4$C$_6$H$_5$ | 4.3 ± 0.42 | 7.1 ± 0.39 | 0.082 ± 0.0026 |
| 61 | (±)- | CONH(CH$_2$)$_5$C$_6$H$_5$ | 1.7 ± 0.15 | 7.9 ± 0.12 | 1.5 ± 0.10 |
| 62 | (±)- | CONH(CH$_2$)$_6$C$_6$H$_5$ | NT | NT | NT |
| 63 | (±)- | CONH(CH$_2$)$_2$—4-Cl—C$_6$H$_4$ | NT | NT | NT |
| 64 | (±)- | CONH(CH$_2$)$_2$—4-CH$_3$O—C$_6$H$_4$ | NT | NT | NT |
| 65 | (±)- | CONH(CH$_2$)$_2$—4-CH$_3$—C$_6$H$_4$ | NT | NT | NT |
| 66 | (±)- | CONH(CH$_2$)$_2$—3,4-Cl$_2$—C$_6$H$_3$ | NT | NT | NT |
| 27 | (±)- | CONH(CH$_2$)$_2$(4-C$_6$H$_4$CH$_2$C$_6$H$_5$) | 0.23 ± 0.032 | 5.9 ± 0.70 | 1.6 ± 0.27 |
| 67 | (−)- | CONHCH(S—CH$_3$)C$_6$H$_5$ | 28 ± 1.4 | >10 μM | 130 ± 4.0 |

TABLE 1-continued

Cyclazocine subseries

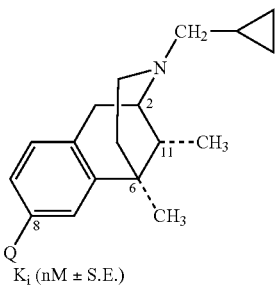

$K_i$ (nM ± S.E.)

| Example # | optical isomer | Q | [$^3$H] DAMGO (μ) | [$^3$H] Naltrindole (δ) | [$^3$H] U69,593 (κ) |
|---|---|---|---|---|---|
| 68 | (−)- | CONHCH(R—CH$_3$)C$_6$H$_5$ | 62 ± 3.3 | >10 μM | 64 ± 4.3 |
| 69 | (±)- | CONHCH$_2$CH$_2$-3-pyr | 120 ± 3.6 | 54 ± 1.3 | 97 ± 3.1 |
| 13 | (±)- | CONH(CH$_2$)$_2$(4-Br-3-pyridinyl) | | | |
| 14 | (±)- | CONHCH$_2$CH$_2$—(4-Br-2-pyr) | | | |

TABLE 2

Keto subseries:

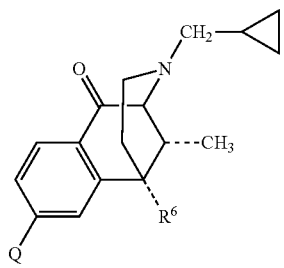

$R^6$ = CH$_3$ (ketocyclazocine)
$R^6$ = CH$_2$CH$_3$ (EKC)

| example | Q = | [$^3$H] DAMGO (μ) | [$^3$H] Naltrindole (δ) | [$^3$H] U69,593 (κ) |
|---|---|---|---|---|
| 20 | CONH(CH$_2$)$_2$(4-C$_6$H$_4$C$_6$H$_5$ (KC) | 3.1 ± 1.3 | 3.9 ± 1.4 | 1.3 ± 0.072 |
| 21 | CONH(CH$_2$)$_2$(4-C$_6$H$_4$C$_6$H$_5$ (EKC) | 4.9 ± 0.20 | 13 ± 2.5 | 5.1 ± 0.18 |

TABLE 3

Other Opioid Parents

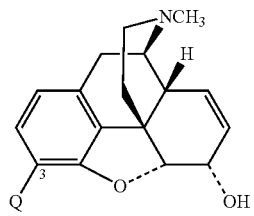

Morphine core

TABLE 3-continued

Other Opioid Parents

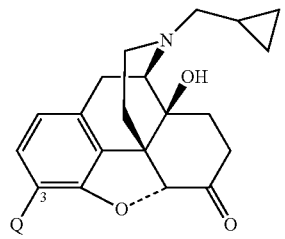

Naltrexone core

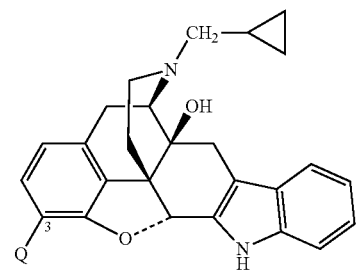

Naltrindole core

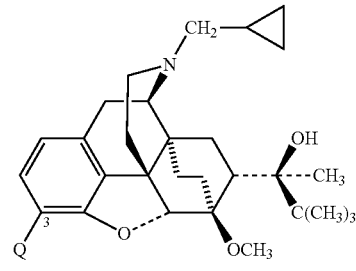

Buprenorphine core

TABLE 3-continued

Other Opioid Parents

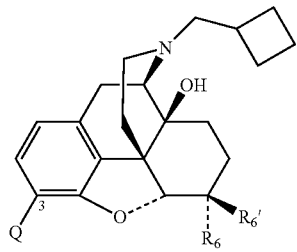

Nalbuphine core

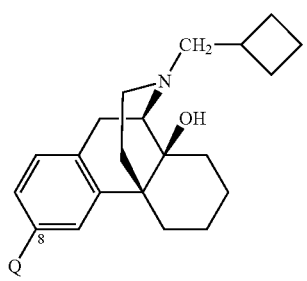

Butorphanol core

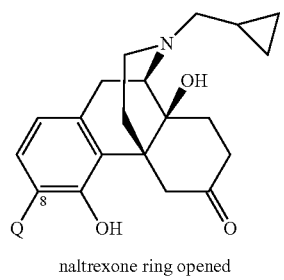

naltrexone ring opened

| example | Q = CONH(CH$_2$)$_2$(4-C$_6$H$_4$C$_6$H$_5$) | [$^3$H] DAMGO (μ) | [$^3$H] Naltrindole (δ) | [$^3$H] U69,593 (κ) |
|---|---|---|---|---|
| 70 | naltrexone | 0.11 ± 0.006 | 11 ± 1.1 | 0.31 ± 0.03 |
| 71 | Q-naltrexone | 1.4 ± 0.12 | 34 ± 4.1 | 22 ± 1.4 |
| 72 | naltrindole | 13 ± 1.1 | 0.13 ± 0.02 | 4.6 ± 0.23 |
| 73 | Q-naltrindole | NT | NT | NT |
| 74 | buprenorphine | 0.21 ± 0.024 | 2.9 ± 0.49 | 0.62 ± 0.073 |
| 75 | Q-buprenorphine | 1.3 ± 0.072 | 16 ± 1.9 | 120 ± 15 |
| 76 | nalbuphine | 1.6 ± 0.37 | 580 ± 80 | 3.0 ± 0.63 |
| 77 | Q-nalbuphine | 5.2 ± 0.07 | 82 ± 3.3 | 82 ± 5.8 |
| 78 | butorphanol | 0.12 ± 0.058 | 12 ± 3.8 | 0.22 ± 0.023 |
| 79 | Q-butorphanol | 0.32 ± 0.048 | 0.45 ± 0.039 | 3.9 ± 0.47 |
| 80 | naltrexone ring opened | 17 ± 4.0 | 130 ± 6.6 | 2.2 ± 0.16 |
| 81 | Q-naltrexone ring opened | 0.71 ± 0.091 | 3.7 ± 0.20 | 1.9 ± 0.15 |

Antinociceptive activity is evaluated by the method described in Jiang et al. [*J. Pharmacol. Exp. Ther.* 264, 1021-1027 (1993), page 1022]. The ED$_{50}$s of compounds of the invention are expected to be under 100 nmol in the mouse acetic acid writhing test when administered i.c.v., and an increase in the duration of action is expected for compounds of the invention compared to their "parents" when given by i.p. administration.

DEFINITIONS

Throughout this specification the terms and substituents retain their definitions.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, cyclopropyl, butyl, s- and t-butyl, cyclobutyl and the like. Preferred alkyl groups are those of C$_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Loweralkoxy refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like. Heteroarylalkyl means an alkyl residue attached to a heteroaryl ring. Examples include, e.g., pyridinylmethyl, pyrimidinylethyl and the like.

Heterocycle means a cycloalkyl or aryl residue in which one to two of the carbons is replaced by a heteroatom such as oxygen, nitrogen or sulfur. Heteroaryls form a subset of heterocycles. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like.

Substituted alkyl, aryl, cycloalkyl, or heterocyclyl refer to alkyl, aryl, cycloalkyl, or heterocyclyl wherein up to three H atoms in each residue are replaced with halogen, hydroxy, loweralkoxy, carboxy, carboalkoxy, carboxamido, cyano, carbonyl, —NO$_2$, —NR$^1$R$^2$; alkylthio, sulfoxide, sulfone, acylamino, amidino, phenyl, benzyl, heteroaryl, phenoxy, benzyloxy, heteroaryloxy, or substituted phenyl, benzyl, heteroaryl, phenoxy, benzyloxy, or heteroaryloxy.

Virtually all of the compounds described herein contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, as well as their racemic and optically pure forms. In general it has been found that the levo isomer of morphinans and benzomorphans is the more potent antinociceptive agent, while the dextro isomer may be useful as an antitussive or antispasmodic agent. Optically active (R)— and (S)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

ABBREVIATIONS

The following abbreviations and terms have the indicated meanings throughout:
Ac=acetyl
BNB=4-bromomethyl-3-nitrobenzoic acid
Boc=t-butyloxy carbonyl
Bu=butyl
c-=cyclo
DAMGO=Tyr-ala-Gly-NMePhe-NHCH$_2$OH
DBU=diazabicyclo[5.4.0]undec-7-ene
DCM=dichloromethane=methylene chloride=CH$_2$Cl$_2$
DEAD=diethyl azodicarboxylate
DIC=diisopropylcarbodiimide
DIEA=N,N-diisopropylethyl amine
DMAP=4-N,N-dimethylaminopyridine
DMF=N,N-dimethylformamide
DMSO=dimethyl sulfoxide
DPPF=1,1'-bis(diphenylphosphino)ferrocene
DVB=1,4-divinylbenzene
EEDQ=2-ethoxy-1-ethoxycarbonyl-1,2-dihydroquinoline
Fmoc=9-fluorenylmethoxycarbonyl
GC=gas chromatography
HATU=O-(7-Azabenzotriazol-1-yl)-1,1,3,3-tetramethyluronium hexafluorophosphate
HOAc=acetic acid
HOBt=hydroxybenzotriazole
Me=methyl
mesyl=methanesulfonyl
MTBE=methyl t-butyl ether
NMO=N-methylmorpholine oxide
PEG=polyethylene glycol
Ph=phenyl
PhOH=phenol
PfP=pentafluorophenol
PPTS=pyridinium p-toluenesulfonate
PyBroP=bromo-tris-pyrrolidino-phosphonium hexafluorophosphate
rt=room temperature
sat'd=saturated
s-=secondary
t-=tertiary
TBDMS=t-butyldimethylsilyl
TFA=trifluoroacetic acid
THF=tetrahydrofuran
TMOF=trimethyl orthoformate
TMS=trimethylsilyl
tosyl=p-toluenesulfonyl
Trt=triphenylmethyl
U69,593=

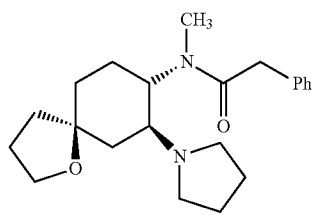

It may happen that residues in the substrate of interest require protection and deprotection during the conversion of the phenol to the desired Q. Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is below, the person of ordinary skill can readily envision those groups that would be suitable as "protecting groups". Suitable groups for that purpose are discussed in standard textbooks in the field of chemistry, such as *Protective Groups in Organic Synthesis* by T. W. Greene [John Wiley & Sons, New York, 1991], which is incorporated herein by reference.

The compounds of the invention are synthesized by one of the routes described below:

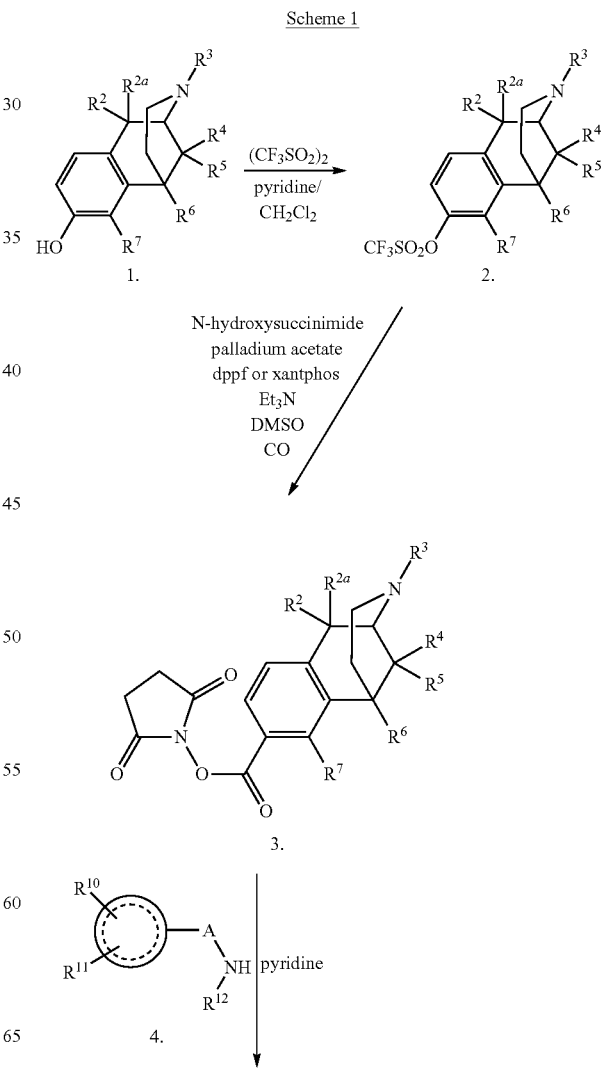

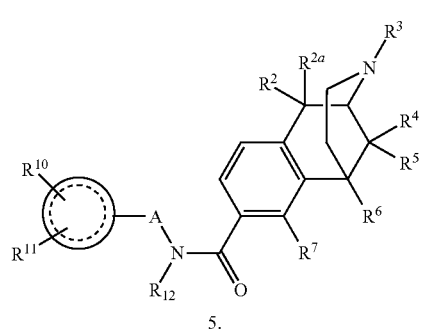

5.

Scheme 2

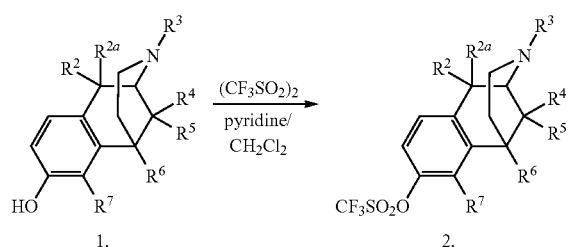

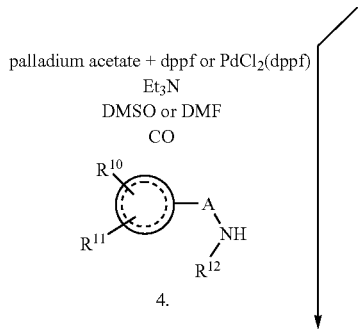

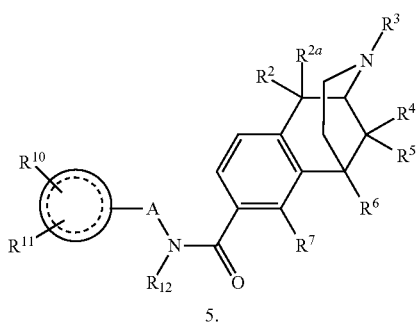

5.

Scheme 3

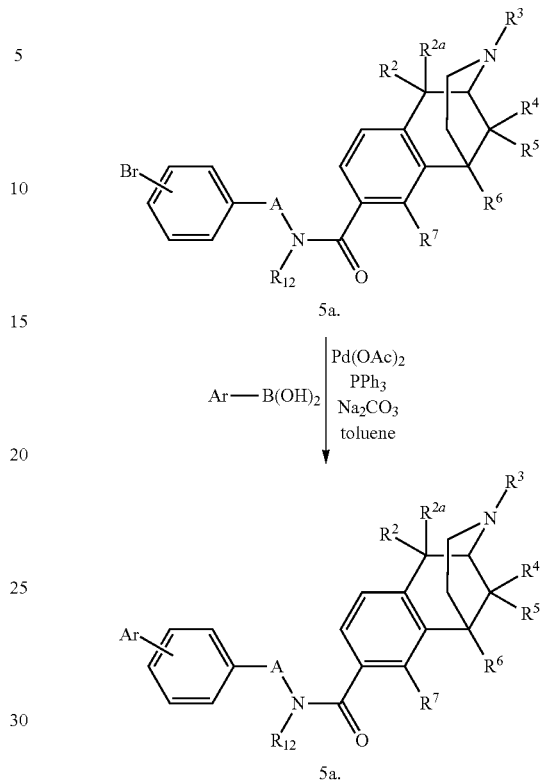

In general, the intermediate N-hydroxysuccinimide ester intermediates (3) shown in scheme 1 are prepared by the processes of U.S. Pat. No. 7,057,0357, the contents of which are incorporated herein by reference. The N-hydroxysuccinimide ester is then reacted with the appropriate arylalkylamine (4) as described below. An alternative, employing direct carbonylation/amidation is shown in Scheme 2. Many diaryl compounds can be prepared by Suzuki coupling, shown in Scheme 3.

Proton NMR spectra and in certain cases $^{13}C$ NMR were obtained on a Varian Unity-300 or 500 NMR spectrometer with tetramethylsilane as an internal reference for samples dissolved in $CDCl_3$. Samples dissolved in $CD_3OD$ and DMSO-$d_6$ were referenced to the solvent. Proton NMR multiplicity data are denoted by s (singlet), d (doublet), t (triplet), q (quartet), m (multiplet), dd (doublet of doublets), and br (broad). Coupling constants are in hertz. Direct insertion probe chemical ionization mass spectral data were obtained on a Shimadzu GC-17A GC-MS mass spectrometer. Direct infusion electrospray ionization (in positively charged ion mode) mass spectral data were obtained on an Agilent 1100 series LC/MSD system (Germany). Melting points were determined on a Meltemp capillary melting point apparatus and were uncorrected. Infrared spectral data were obtained on a Perkin-Elmer Paragon 1000 FT-IR spectrophotometer. Optical rotation data was obtained from a Perkin-Elmer 241 polarimeter. The assigned structure of all test compounds and intermediates were consistent with the data. Carbon, hydrogen, and nitrogen elemental analyses for all novel targets were performed by Quantitative Technologies Inc., Whitehouse, N.J., and were within ±0.4% of theoretical values except as noted; the presence of water or other solvents was confirmed by proton NMR. Reactions were generally performed in an argon or nitrogen atmosphere. Commercially purchased chemicals were used without purification unless otherwise noted. The following reagents were purchased from Aldrich Chemical Company: N-hydroxysuccinimide, phenethylamine, 3-phenyl-1-propylamine, 4-aminobiphenyl, palladium acetate, 4-phenylbenzylamine and benzyl amine. The following reagent was purchased from Trans World Chemicals: 2-(4-biphenyl ethylamine). The following reagents were purchased from Strem Chemicals, Incorporated: 1,1'-bis(diphenyl-phosphino)ferrocene (dppf) and dichloro[1,1'-bis(diphenylphosphino)-ferrocene]palladium (II) dichloromethane adduct [PdCl$_2$(dppf)]. Pyridine was distilled from KOH. DMF and DMSO were distilled over CaH$_2$ under reduced pressure. Silica gel (Bodman Industries, ICN SiliTech 2-63 D 60A, 230-400 Mesh) was used for all flash chromatography. Amines were purchased from Aldrich Chemical Company and used as received unless otherwise indicated. Toluene and Et$_2$O were distilled from sodium metal. THF was distilled from sodium/benzophenone ketyl. Pyridine was distilled from KOH. Methylene chloride was distilled from CaH$_2$. DMF and DMSO were distilled from CaH$_2$ under reduced pressure. Methanol was dried over 3± molecular sieves prior to use. Silica gel (Bodman Industries, ICN SiliTech 2-63 D 60A, 230-400 Mesh) was used for flash column chromatography.

(±)-1-[[[3-(Cyclopropylmethyl)-1,2,3,4,5,6-hexahydro-cis-6,11-dimethyl-2,6-methano-3-benzazocin-8-yl]carbonyl]oxy]-2,5-Pyrrolidinedione [(3) $R^3$=CH$_2$c-C$_3$H$_5$; $R^2$, $R^{2a}$, $R^4$ and $R^7$=H; $R^5$ and $R^6$=CH$_3$.] To a flask charged with triflate [(2) $R^3$=CH$_2$c-C$_3$H$_5$; $R^2$, $R^{2a}$, $R^4$ and $R^7$=H; $R^5$ and $R^6$=CH$_3$] (403 mg, 1.00 mmol), N-hydroxy succinimide (230 mg, 2.00 mmol) palladium acetate (22.4 mg, 0.10 mmol) and dppf (55.4 mg, 0.10 mmol) was added triethyl amine (0.28 mL, 2.00 mmol). The reaction was equipped with a condenser and sealed with a septum and a balloon. The whole system was vacuumed and backfilled with nitrogen for three cycles. DMSO (1 mL) was added via syringe. Then it was vacuumed again and backfilled with a mixture of carbon monoxide. The resulting mixture was heated at 70° C. for 8.5 h. The cooled reaction mixture was diluted with ethyl acetate (30 mL), washed with water, and brine. The organic phase was dried over sodium sulfate, filtered, and concentrated to give a brown oil, which was purified by flash chromatography (Ethyl acetate:Acetone:Hexane:Et$_3$N 2:1:0.4:0.03) to give 3 as a white foam (217 mg, 0.55 mmol, 55%): $^1$H NMR (500 MHz, CDCl$_3$) δ7.96 (d, 1H, J=1.5 Hz), 7.82 (dd, 1H, J$_1$=1.5 Hz, J$_2$=8.1 Hz), 7.17 (d, 1H, J=8.1 Hz), 3.19 (m, 1H), 2.97 (d, 1H, J=19.5 Hz), 2.85 (s, 4H), 2.73 (m, 2H), 2.44 (dd, 1H, J$_1$=6.4 Hz, J$_2$=12.7 Hz), 2.33 (dd, 1H, J$_1$=6.6 Hz, J$_2$=12.4 Hz), 1.93 (m, 1H), 1.84 (d, 2H, J=8.5 Hz), 1.35 (s, 3H), 1.27 (m, 1H), 0.83 (m, 1H), 0.79 (d, 3H, J=7.1 Hz), 0.48 (m, 2H), 0.08 (m, 2H). MS (ESI) m/z 397 (M+H)$^+$; Anal. Calcd. for C$_{23}$H$_{28}$N$_2$O$_4$.0.5H$_2$O: C, 68.20; H, 7.20; N, 6.90. Found: C, 68.04; H, 6.92; N, 7.12.

(±)-3-(Cyclopropylmethyl)-1,2,3,4,5,6-hexahydro-cis-6,11-dimethyl-N-(2-[1,1'-biphenyl]-4-ylethyl)-2,6-methano-3-benzazocine-8-carboxamide (15).

Method A. Conditions similar to those previously reported by Wentland et al. [*Bioorgan. Med. Chem. Lett.* 2001, 11, 623-626] were used. A solution of (±)-3 (140 mg, 0.35 mmol) and 2-(4-biphenyl ethylamine) (84 mg, 0.42 mmol) in 2.5 mL of dry pyridine was stirred at room temperature for 48 h. The solvent was removed in vacuo and the residue was taken up in methylene chloride (40 mL), washed once with saturated sodium bicarbonate solution, water, and brine. The organic phase was dried over sodium sulfate, filtered, and concentrated to give a brown residue, which was purified by flash chromatography (CH$_2$Cl$_2$:CH$_3$OH:NH$_4$OH 15:1:0.1) to give 15 as an off-white foam (110 mg, 0.23 mmol, 66%). $^1$H NMR (500 MHz, CDCl$_3$) δ7.66 (d, 1H, J=1.5 Hz), 7.57 (dd, 2H, J$_1$=1.3 Hz, J$_2$=7.5 Hz), 7.55 (d, 2H, J=8.5 Hz), 7.43 (t, 2H, J=7.75 Hz), 7.39 (dd, 1H, J$_1$=1.8 Hz, J$_2$=7.75 Hz), 7.34 (t, 1H, J=7.5 Hz), 7.31 (d, 2H, J=8 Hz), 7.08 (d, 1H, J=8 Hz), 6.32 (bt, 1H, J=5.75 Hz), 3.72 (q, 2H, J=6.7 Hz), 3.14 (m, 1H), 2.97 (t, 2H, J=1.5 Hz), 2.93 (d, 1H, J=18.5 Hz), 2.70 (m, 2H), 2.45 (dd, 1H, J$_1$=6.3 Hz, J$_2$=12.75 Hz), 2.34 (dd, 1H, J$_1$=6.75 Hz, J$_2$=12.75 Hz), 1.93 (m, 3H), 1.39 (s, 3H), 1.32 (d, 1H, J=9.5), 0.87 (m, 1H), 0.81 (d, 3H, J=7.0 Hz), 0.50 (dd, 2H, J$_1$=1.5 Hz, J$_2$=8.0 Hz), 0.12 (m, 2H). MS (ESI) m/z 479 (M+H)$^+$; Anal. Calcd. for C$_{33}$H$_{38}$N$_2$O.1.0H$_2$O: C, 79.80; H, 8.12; N, 5.64. Found: C, 79.72; H, 8.07; N, 5.96.

(±)-3-(Cyclopropylmethyl)-1,2,3,4,5,6-hexahydro-cis-6,11-dimethyl-N-(2-phenylethyl)-2,6-methano-3-benzazocine-8-carboxamide (11). This compound was prepared using Method A and phenethylamine. Off-white foam (93 mg, 0.231 mmol, 83%). $^1$H NMR (500 MHz, CDCl$_3$) δ7.61 (d, 1H, J=2.0 Hz), 7.35 (m, 3H), 7.26 (m, 3H), 7.08 (d, 1H, J=8 Hz), 6.07 (bt, 1H, J=5.0 Hz), 3.71 (q, 2H, J=6.5 Hz), 3.16 (m, 1H), 2.94 (m, 3H), 2.70 (m, 2H), 2.47 (m, 1H), 2.32 (m, 1H), 1.93 (m, 3H), 1.40 (s, 3H), 1.33 (d, 1H, J=11.5), 0.87 (m, 1H), 0.82 (d, 3H, J=7.0 Hz), 0.52 (d, 2H, J=8.0 Hz), 0.11 (m, 2H); MS (ESI) m/z 403 (M+H)$^+$; Anal. Calcd. for C$_{27}$H$_{34}$N$_2$O.0.5H$_2$O: C, 78.79; H, 8.57; N, 6.81. Found: C, 78.90; H, 8.55; N, 6.86.

(±)-3-(Cyclopropylmethyl)-1,2,3,4,5,6-hexahydro-cis-6,11-dimethyl-N-(3-phenylpropyl)-2,6-methano-3-benzazocine-8-carboxamide (12). This compound was prepared using Method A and 3-phenyl-1-propylamine. Off-white foam (72 mg, 0.174 mmol, 68%). $^1$H NMR (500 MHz, CDCl$_3$) δ7.66 (d, 1H, J=1.5 Hz), 7.30 (m, 3H), 7.21 (m, 3H), 7.09 (d, 1H, J=8 Hz), 6.02 (bt, 1H, J=5.5 Hz), 3.50 (q, 2H, J=6.8 Hz), 3.15 (m, 1H), 2.95 (d, 1H, J=19.0 Hz), 2.71 (m, 4H), 2.46 (m, 1H), 2.32 (m, 1H), 1.94 (m, 5H), 1.42 (s, 3H), 1.34 (d, 1H, J=9.75), 0.87 (m, 1H), 0.82 (d, 3H, J=7.0 Hz), 0.51 (d, 2H, J=8.0 Hz), 0.11 (m, 2H); MS (ESI) m/z 417 (M+H)$^+$; Anal. Calcd. for C$_{28}$H$_{36}$N$_2$O.0.33H$_2$O: C, 79.58; H, 8.75; N, 6.63. Found: C, 79.71; H, 8.75; N, 6.66.

(−)-3-(Cyclopropylmethyl)-1,2,3,4,5,6-hexahydro-cis-6,11-dimethyl-N-(2-[1,1'-biphenyl]-4-ylethyl)-2,6-methano-3-benzazocine-8-carboxamide [(−)-16]. Method B. Conditions similar to those previously reported were used. 2-(4-Biphenyl ethylamine) (85 mg, 0.43 mmol) PdCl$_2$(dppf) (16 mg, 0.02 mmol) were added to a two-neck flask charged with triflate ester of (−)-cyclazocine[5] (158 mg, 0.39 mmol). The reaction was equipped with a condenser and sealed with a septum and a balloon. The whole system was vacuumed and backfilled with nitrogen for three cycles. DMF (2 mL) and triethylamine (0.09 mL, 0.62 mmol) were added via syringe. Then it was vacuumed again and backfilled with a mixture of carbon monoxide. The resulting mixture was heated at 70° C. for 18 h. The cooled reaction mixture was diluted with ethyl acetate (30 mL), washed with saturated bicarbonate solution, water, and brine. The organic phase was dried over sodium sulfate, filtered, and concentrated to give a black oil, which was purified by flash chromatography (CH$_2$Cl$_2$:CH$_3$OH:NH$_4$OH 25:1:0.1) to give (−)-16 as an off-white foam (100 mg, 0.21 mmol, 53%). $^1$H NMR (300 MHz, CDCl$_3$) δ7.68 (s, 1H), 7.57 (m, 4H), 7.43 (m, 3H), 7.33 (m, 3H), 7.08 (d, 1H, J=7.8Hz), 6.34 (bt, 1H, J=6.0 Hz), 3.73 (q, 2H, J=6.0 Hz), 3.16 (m, 1H), 2.94 (m, 3H), 2.71 (m, 2H), 2.48 (m, 1H), 2.31 (m, 1H), 1.93 (m, 3H), 1.40 (s, 3H), 1.32 (m, 1H), 0.87 (m, 1H), 0.82 (d, 3H, J=7.2 Hz), 0.51 (d, 2H, J=6.6 Hz), 0.11 (m, 2H). MS (ESI) m/z 479 (M+H)$^+$; Anal. Calcd. for C$_{33}$H$_{38}$N$_2$O.1.25H$_2$O: C, 79.08; H, 8.14; N, 5.59. Found: C, 79.23; H, 7.84; N, 5.57. For (−)-16: $[\alpha]^{25}_D$=−69.1° (c=0.75, acetone).

(+)-3-(Cyclopropylmethyl)-1,2,3,4,5,6-hexahydro-cis-6,11-dimethyl-N-(2-[1,1'-biphenyl]-4-ylethyl)-2,6-methano-3-benzazocine-8-carboxamide [(+)-17]. This compound was prepared using Method B and triflate ester of (+)-cyclazocine.5 Off-white foam (90 mg, 0.19 mmol, 49%). $^1$H NMR (500 MHz, CDCl$_3$) δ 7.68 (s, 1H), 7.57 (d, 2H, J=7.5 Hz), 7.55 (d, 2H, J=7.5 Hz) 7.42 (m, 3H), 7.32 (m, 3H), 7.07 (d, 1H, J=8.0 Hz), 6.40 (bt, 1H), 3.72 (q, 2H, J=6.0 Hz), 3.13 (m, 1H), 2.94 (m, 3H), 2.69 (m, 2H), 2.45 (dd, 1H, J$_1$=6.5 Hz, J$_2$=13.0 Hz), 2.30 (dd, 1H, J$_1$=6.5 Hz, J$_2$=12.5 Hz), 1.93 (m, 3H), 1.39 (s, 3H), 1.32 (m, 1H), 0.87 (m, 1H), 0.81 (d, 3H, J=7.0 Hz), 0.50 (d, 2H, J=8.0 Hz), 0.11 (m, 2H). MS (ESI) m/z 479 (M+H)$^+$; Anal. Calcd. for C$_{33}$H$_{38}$N$_2$O.0.67H$_2$O: C, 80.78; H, 8.07; N, 5.71. Found: C, 80.96; H, 8.13; N, 5.45. For (+)-17: $[\alpha]^{25}_D$=+81.3° (c=1.02, acetone).

3-[1,1'-biphenyl]-4-propylamine. To a vigorously stirred solution of 4-biphenylacrylamide (440 mg, 1.97 mmol) in 10 mL of THF under nitrogen atmosphere was added 1.0 M lithium alumina hydride solution in THF (4.0 mL, 4.0 mmol). The resulting mixture was stirred for 2 h at reflux. The reaction was then cooled in an ice bath, quenched with water, diluted with ethyl acetate and filtered. The filtrate was washed with saturated bicarbonate solution, water, and brine. The organic phase was dried over magnesium sulfate, filtered, and concentrated to give an oil, which was purified by flash chromatography (CH$_2$Cl$_2$:CH$_3$OH:NH$_4$OH 10:1:0.1) to give 3-[1,1'-biphenyl]-4-propylamine as a clear oil (147 mg, 0.66 mmol, 34%): $^1$H NMR (300 MHz, CDCl$_3$) δ 7.59 (d, 2H, J=7.5 Hz), 7.53 (d, 2H, J=7.8 Hz), 7.44 (t, 2H, J=7.65 Hz), 7.33 (m, 1H), 7.27 (d, 2H, J=7.5 Hz), 2.77 (b, 2H), 2.71 (t, 2H, J=7.65 Hz), 1.99 (b, 2H), 1.82 (m, 2H); MS (ESI) m/z 212 (M+H)$^+$; Anal. Calcd. for C$_{15}$H$_{17}$N.

(±)-3-(Cyclopropylmethyl)-1,2,3,4,5,6-hexahydro-cis-6,11-dimethyl-N-(3-[1,1'-biphenyl]-4-ylpropyl)-2,6-methano-3-benzazocine-8-carboxamide (18). This compound was prepared using Method B and 3-[1,1'-biphenyl]-4-propylamine. Off-white foam (250 mg, 0.51 mmol, 63%). $^1$H NMR (500 MHz, CDCl$_3$) δ 7.68 (s, 1H), 7.57 (d, 2H, J=7.5 Hz), 7.52 (d, 2H, J=7.5 Hz) 7.43 (t, 2H, J=7.75 Hz), 7.32 (m, 4H), 7.05 (d, 1H, J=7.5 Hz), 6.09 (bt, 1H), 3.52 (q, 2H, J=6.7 Hz), 3.13 (m, 1H), 2.93 (d, 1H, J=19 Hz), 2.77 (t, 2H, J=7.75 Hz), 2.67 (m, 2H), 2.45 (dd, 1H, J$_1$=6.0 Hz, J$_2$=12.5 Hz), 2.30 (dd, 1H, J$_1$=6.75 Hz, J$_2$=12.25 Hz), 1.93 (m, 5H), 1.41 (s, 3H), 1.32 (m, 1H), 0.85 (m, 1H), 0.81 (d, 3H, J=7.5 Hz), 0.51 (d, 2H, J=8.0 Hz), 0.10 (m, 2H). MS (ESI) m/z 493 (M+H)$^+$; Anal. Calcd. for C$_{34}$H$_{40}$N$_2$O.0.75H$_2$O: C, 80.67; H, 8.26; N, 5.53. Found: C, 80.78; H, 8.12; N, 5.51.

(±)-3-(Cyclopropylmethyl)-1,2,3,4,5,6-hexahydro-cis-6,11-dimethyl-N-(2-[1,1'-biphenyl]-4-ylethyl)-N-methyl-2,6-methano-3-benzazocine-8-carboxamide (19). This compound was prepared using Method B and N-methyl-[1,1'-biphenyl]-4-ethanamine. Off-white foam (190 mg, 0.39 mmol, 60%). $^1$H NMR (500 MHz, CDCl$_3$) δ 7.56 (m, 4H), 7.43 (m, 3H), 7.39 (m, 1H), 7.33 (t, 2H, J=6.75 Hz), 7.22 (s, 1H), 7.05 (d, 1H, J=7.5 Hz), 3.80 (b, 1H), 3.48 (b, 1H), 3.14 (b, 3H), 3.04 (b, 1H), 2.90 (m, 3H), 2.70 (m, 2H), 2.47 (m, 1H), 2.32 (m, 1H), 1.93 (m, 3H), 1.35 (s, 3H), 1.30 (d, 1H, J=12.5), 0.84 (m, 1H), 0.84 (d, 3H, J=6.5 Hz), 0.51 (d, 2H, J=7.5 Hz), 0.12 (m, 2H). MS (ESI) m/z 493 (M+H)$^+$; Anal. Calcd. for C$_{34}$H$_{40}$N$_2$O.0.13H$_2$O: C, 82.51; H, 8.20; N, 5.66. Found: C, 82.33; H, 8.07; N, 5.69.

(±)-3-(Cyclopropylmethyl)-6-ethyl-1,2,3,4,5,6-hexaahydro-cis-11-methyl-N-(2-[1,1'-biphenyl]-4-ylethyl)-1-oxo-2,6-methano-3-benzazocine-8-carboxamide (21). This compound was prepared using Method B with the triflate ester of EKC and 2-(4-biphenyl ethylamine). Off-white foam (200 mg, 0.39 mmol, 61%). $^1$H NMR (500 MHz, CDCl$_3$) δ 8.00 (d, 1H, J=8.0 Hz), 7.82 (s, 1H), 7.58 (m, 4H), 7.51 (d, 2H, J=8.0 Hz) 7.44 (t, 2H, J=7.5 Hz), 7.33 (m, 3H), 6.19 (bt, 1H), 3.77 (q, 2H, J=6.5 Hz), 3.32 (d, 1H, J=8.0 Hz), 3.00 (t, 2H, J=6.75 Hz) 2.92 (dd, 1H, J$_1$=3.75 Hz, J$_2$=12.25 Hz), 2.65 (dd, 2H, J$_1$=5.75 Hz, J$_2$=8.25 Hz), 2.36 (m, 1H), 2.29 (m, 1H), 2.10 (m, 1H), 1.97 (dd, 1H, J$_1$=7.5 Hz, J$_2$=13.0 Hz), 1.90 (m, 1H), 1.82 (m, 1H), 1.24 (d, 1H, J=12.0 Hz), 1.05 (t, 3H, J=7.75 Hz), 0.87 (m, 1H), 0.79 (d, 3H, J=7.0 Hz), 0.48 (m, 2H), 0.26 (m, 1H), 0.01 (m, 1H). MS (ESI) m/z 507 (M+H)$^+$; Anal. Calcd. for C$_{34}$H$_{38}$N$_2$O$_2$.1.35H$_2$O: C, 76.91; H, 7.73; N, 5.28. Found: C, 76.89; H, 7.48; N, 4.89.

(±)-3-(Cyclopropylmethyl)-1,2,3,4,5,6-hexahydro-cis-6,11-dimethyl-N-(2-(biphenyl-3-yl)ethyl)-2,6-methano-3-benzazocine-8-carboxamide (25). Method B Phenylboronic acid (38 mg, 0.31 mmol), 10 (100 mg, 0.21 mmol), palladium acetate (5 mg, 0.02 mmol), triphenylphosphine (21 mg, 0.08 mmol), 4N sodium carbonate (0.52 mmol) and toluene were places in a microwave vial, sealed and heated at 120° C. for 20 min. The cooled reaction mixture was diluted with ethyl acetate (30 mL), washed with saturated bicarbonate solution, water, and brine. The organic phase was dried over sodium sulfate, filtered, and concentrated to give a black oil, which was purified by flash chromatography (CH$_2$Cl$_2$:CH$_3$OH:NH$_4$OH 25:1:0.1) to give 5 as an white foam (80 mg, 80%). $^1$H NMR (500 MHz, CDCl$_3$) δ 7.61 (s, 1H), 7.56 (d, 2H, J=7.5 Hz), 7.47 (m, 2H), 7.42 (m, 4H), 7.34 (t, 1H, J=7.3 Hz), 7.23 (d, 1H, J=7.5 Hz), 7.07 (d, 1H, J=7.5 Hz), 6.18 (t, 1H, J=5.7 Hz), 3.72 (q, 2H, J=6.7 Hz), 3.14 (s, 1H), 2.97 (t, 2H, J=1.5 Hz), 2.93 (d, 1H, J=18.5 Hz), 2.70 (m, 2H), 2.45 (dd, 1H, J$_1$=6.3 Hz, J$_2$=12.75 Hz), 2.34 (dd, 1H, J$_1$=6.75 Hz, J$_2$=12.75 Hz), 1.93 (m, 3H), 1.39 (s, 3H), 1.27 (d, 1H, J=11.5), 0.87 (m, 1H), 0.81 (d, 3H, J=7.0 Hz), 0.50 (dd, 2H, J$_1$=1.5 Hz, J$_2$=8.0 Hz), 0.12 (m, 2H). MS (ESI) m/z 479 (M+H)+; Anal. Calcd. for C$_{33}$H$_{38}$N$_2$O.1.0H$_2$O: C, 79.80; H, 8.12; N, 5.64. Found: C, 79.66; H, 7.85; N, 5.62.

(±)-3-(Cyclopropylmethyl)-1,2,3,4,5,6-hexahydro-cis-6,11-dimethyl-N-(2-(biphenyl-2-yl)ethyl)-2,6-methano-3-benzazocine-8-carboxamide (26). Prepared using Method B. White foam (70 mg, 70%). $^1$H NMR (300 MHz, CDCl$_3$) δ 7.58 (s, 1H), 7.2-7.4 (m, 10H), 7.06 (d, 1H, J=7.8 Hz), 5.97 (t, 1H, J=5.7 Hz), 3.50 (q, 2H, J=6.0 Hz), 3.14 (s, 1H), 2.94 (m, 3H), 2.70 (m, 2H), 2.44 (dd, 1H, J$_1$=6 Hz, J$_2$=13 Hz), 2.31 (dd, 1H, J$_1$=6 Hz, J$_2$=13 Hz), 1.90 (m, 3H), 1.40 (s, 3H), 1.31 (m, 1H), 0.88 (m, 1H), 0.82 (d, 3H, J=7.0 Hz), 0.50 (d, 2H, J=8.1 Hz), 0.12 (m, 2H). MS (ESI) m/z 479 (M+H)+; Anal. Calcd. for C$_{33}$H$_{38}$N$_2$O.0.75H$_2$O: C, 80.53; H, 8.09; N, 5.69. Found: C, 80.43; H, 8.10; N, 5.79.

(±)-3-(Cyclopropylmethyl)-1,2,3,4,5,6-hexahydro-cis-6,11-dimethyl-N-(4-benzylphenethyl)-2,6-methano-3-benzazocine-8-carboxamide (27). Prepared using Method A and 2-(4-benzylphenyl)ethanamine. White foam (83 mg, 42%). $^1$H NMR (300 MHz, CDCl$_3$) δ 7.60 (s, 1H), 7.35 (d, 1H, J=7.8 Hz), 7.28 (m, 2H), 7.17 (m, 7H), 7.07 (d, 1H, J=8.1 Hz), 6.08 (t, 1H, J=6 Hz), 3.96 (s, 2H), 3.67 (q, 2H, J=6.5 Hz), 3.13 (s, 1H), 2.94 (d, 1H, J=18.3 Hz), 2.89 (t, 2H, J=6.9 Hz), 2.68 (m, 2H), 2.46 (dd, 1H, J$_1$=6.5 Hz, J$_2$=12.5 Hz), 2.31 (dd, 1H, J$_1$=6.6 Hz, J$_2$=12.9 Hz), 1.90 (m, 3H), 1.38 (s, 3H), 1.30 (d, 1H, J=11.1 Hz), 0.85 (m, 1H), 0.82 (d, 3H, J=7.0 Hz), 0.51 (d, 2H, J=8.0 Hz), 0.09 (m, 2H). MS (ESI) m/z 493 (M+H)+; Anal. Calcd. for C$_{34}$H$_{40}$N$_2$O.0.4H$_2$O: C, 81.69; H, 8.23; N, 5.60. Found: C, 81.59; H, 8.26; N, 5.57.

(±)-3-(Cyclopropylmethyl)-1,2,3,4,5,6-hexahydro-cis-6,11-dimethyl-N-(4-bromophenethyl)-2,6-methano-3-benzazocine-8-carboxamide (29). Prepared using Method A and 2-(4-bromophenyl)ethanamine. Off-white foam (60 mg, 50%). ¹H NMR (300 MHz, CDCl₃) δ 7.63 (s, 1H), 7.42 (d, 2H, J=8.3 Hz), 7.35 (d, 1H, J=8.1 Hz), 7.09 (d, 2H, J=8.3 Hz), 7.07 (d, 1H, J=7.3 Hz), 6.21 (t, 1H, J=6 Hz), 3.65 (q, 2H, J=6.3 Hz), 3.15 (m, 1H), 2.95 (d, 1H, J=19 Hz), 2.87 (t, 2H, J=7.0 Hz), 2.7 (m, 2H), 2.46 (dd, 1H, $J_1$=6.4 Hz, $J_2$=12.7 Hz), 2.31 (dd, 1H, $J_1$=6.8 Hz, $J_2$=12.4 Hz), 1.90 (m, 3H), 1.39 (s, 3H), 1.31 (m, 1H), 0.89 (m, 1H), 0.81 (d, 3H, J=7.2 Hz), 0.50 (m, 2H), 0.10 (m, 2H). MS (ESI) m/z 481, 483 (M+H)+; Anal. Calcd. for $C_{27}H_{33}N_2OBr.0.1H_2O$: C, 67.10; H, 6.92; N, 5.80. Found: C, 67.04; H, 6.80; N, 5.74.

(±)-3-(Cyclopropylmethyl)-1,2,3,4,5,6-hexahydro-cis-6,11-dimethyl-N-(3-bromophenethyl)-2,6-methano-3-benzazocine-8-carboxamide (20). Prepared using Method A and 2-(3-bromophenyl)ethanamine. Off-white foam (159 mg, 53%). ¹H NMR (300 MHz, CDCl₃) δ 7.62 (s, 1H), 7.42 (m, 3H), 7.2 (m, 2H), 7.09 (d, 2H, J=7.8 Hz), 6.1 (t, 1H, J=6 Hz), 3.68 (q, 2H, J=6.1 Hz), 3.15 (m, 1H), 2.95 (d, 1H, J=19 Hz), 2.91 (t, 2H, J=7.1 Hz), 2.7 (m, 2H), 2.46 (dd, 1H, $J_1$=6.4 Hz, $J_2$=12.7 Hz), 2.31 (dd, 1H, $J_1$=6.8 Hz, $J_2$=12.4 Hz), 1.90 (m, 3H), 1.41 (s, 3H), 1.32 (m, 1H), 0.89 (m, 1H), 0.82 (d, 3H, J=7.2 Hz), 0.50 (m, 2H), 0.11 (m, 2H). MS (ESI) m/z 481, 483 (M+H)+; Anal. Calcd. for $C_{27}H_{33}N_2OBr.0.1H_2O$: C, 67.10; H, 6.92; N, 5.80. Found: C, 67.00; H, 6.94; N, 5.72.

(±)-3-(Cyclopropylmethyl)-1,2,3,4,5,6-hexahydro-cis-6,11-dimethyl-N-(2-bromophenethyl)-2,6-methano-3-benzazocine-8-carboxamide (31). Prepared using Method A and 2-(2-bromophenyl)ethanamine. Off-white foam (150 mg, 56%). ¹H NMR (300 MHz, CDCl₃) δ 7.64 (s, 1H), 7.58 (d, 1H, J=7.8 Hz), 7.40 (d, 1H, J=7.8 Hz), 7.28 (m, 2H), 7.1 (m, 2H), 6.16 (t, 1H, J=6 Hz), 3.73 (q, 2H, J=6.6 Hz), 3.15 (m, 1H), 3.11 (t, 2H, J=7.0 Hz), 2.95 (d, 1H, J=19 Hz), 2.7 (m, 2H), 2.46 (dd, 1H, $J_1$=6.4 Hz, $J_2$=12.7 Hz), 2.31 (dd, 1H, $J_1$=6.8 Hz, $J_2$=12.4 Hz), 1.90 (m, 3H), 1.42 (s, 3H), 1.32 (m, 1H), 0.89 (m, 1H), 0.83 (d, 3H, J=7.2 Hz), 0.51 (m, 2H), 0.11 (m, 2H). MS (ESI) m/z 481, 483 (M+H)+; Anal. Calcd. for $C_{27}H_{33}N_2OBr$: C, 67.35; H, 6.91; N, 5.82. Found: C, 67.22; H, 6.91; N, 5.78.

(±)-3-(Cyclopropylmethyl)-1,2,3,4,5,6-hexahydro-cis-6,11-dimethyl-N-(4-phenoxyphenethyl)-2,6-methano-3-benzazocine-8-carboxamide (33). Prepared using Method A and 2-(4-phenoxyphenyl)ethanamine. Off-white foam (145 mg, 67%). ¹H NMR (500 MHz, CDCl₃) δ 7.63 (s, 1H), 7.37 (d, 1H, J=8 Hz), 7.33 (t, 2H, J=8 Hz), 7.20 (d, 2H, J=8.5 Hz), 7.09 (m, 2H), 6.99 (d, 2H, J=8 Hz), 6.96 (d, 2H, J=8 Hz), 6.16 (t, 1H, J=6 Hz), 3.68 (q, 2H, J=6.5 Hz), 3.14 (m, 1H), 2.94 (d, 1H, J=20 Hz), 2.91 (t, 2H, J=6.9 Hz), 2.69 (m, 2H), 2.46 (dd, 1H, $J_1$=6.5 Hz, $J_2$=12.5 Hz), 2.31 (dd, 1H, $J_1$=6.5 Hz, $J_2$=12.5 Hz), 1.90 (m, 3H), 1.40 (s, 3H), 1.31 (d, 1H, J=10 Hz), 0.86 (m, 1H), 0.82 (d, 3H, J=7.0 Hz), 0.50 (d, 2H, J=8.0 Hz), 0.10 (m, 2H). MS (ESI) m/z 495 (M+H)+; Anal. Calcd. for $C_{33}H_{38}N_2O_2.0.25H_2O$: C, 79.40; H, 7.77; N, 5.61. Found: C, 79.37; H, 7.89; N, 5.77.

(±)-3-(Cyclopropylmethyl)-1,2,3,4,5,6-hexahydro-cis-6,11-dimethyl-N-(3-phenoxyphenethyl)-2,6-methano-3-benzazocine-8-carboxamide (34). Prepared using Method A and 2-(3-phenoxyphenyl)ethanamine. Off-white foam (124 mg, 63%). ¹H NMR (500 MHz, CDCl₃) δ 7.63 (s, 1H), 7.35 (d, 1H, J=8 Hz), 7.29 (m, 3H), 7.09 (m, 2H), 6.98 (m, 3H), 6.88 (m, 2H), 6.15 (t, 1H, J=6 Hz), 3.68 (q, 2H, J=6.5 Hz), 3.14 (m, 1H), 2.94 (d, 1H, J=21.5 Hz), 2.89 (t, 2H, J=7.0 Hz), 2.69 (m, 2H), 2.46 (dd, 1H, $J_1$=6.3 Hz, $J_2$=12.8 Hz), 2.31 (dd, 1H, $J_1$=6.5 Hz, $J_2$=12.5 Hz), 1.90 (m, 3H), 1.40 (s, 3H), 1.32 (d, 1H, J=10 Hz), 0.85 (m, 1H), 0.82 (d, 3H, J=7.0 Hz), 0.51 (d, 2H, J=8.0 Hz), 0.10 (m, 2H). MS (ESI) m/z 495 (M+H)+; Anal. Calcd. for $C_{33}H_{38}N_2O_2.0.2H_2O$: C, 79.55; H, 7.77; N, 5.62. Found: C, 79.65; H, 7.83; N, 5.53.

(±)-3-(Cyclopropylmethyl)-1,2,3,4,5,6-hexahydro-cis-6,11-dimethyl-N-(2-phenoxyphenethyl)-2,6-methano-3-benzazocine-8-carboxamide (35). Prepared using Method A and 2-(2-phenoxyphenyl)ethanamine. Off-white foam (152 mg, 65%). ¹H NMR (300 MHz, CDCl₃) δ 7.65 (s, 1H), 7.40 (d, 1H, J=7.8 Hz), 7.3 (m, 3H), 7.2 (m, 1H), 7.08 (m, 3H), 6.91 (m, 3H), 6.36 (t, 1H, J=6 Hz), 3.71 (q, 2H, J=6.3 Hz), 3.14 (m, 1H), 2.97 (t, 2H, J=6.75 Hz), 2.95 (d, 1H, J=18.9 Hz), 2.7 (m, 2H), 2.46 (dd, 1H, $J_1$=6.2 Hz, $J_2$=12.8 Hz), 2.31 (dd, 1H, $J_1$=6.6 Hz, $J_2$=12.9 Hz), 1.90 (m, 3H), 1.40 (s, 3H), 1.32 (m, 1H), 0.86 (m, 1H), 0.82 (d, 3H, J=7.2 Hz), 0.51 (d, 2H, J=8.1 Hz), 0.11 (m, 2H). MS (ESI) m/z 495 (M+H)+; Anal. Calcd. for $C_{33}H_{38}N_2O_2.0.2H_2O$: C, 79.55; H, 7.77; N, 5.62. Found: C, 79.54; H, 7.86; N, 5.69.

(±)-3-(Cyclopropylmethyl)-1,2,3,4,5,6-hexahydro-cis-6,11-dimethyl-N-(2-(naphthalen-2-yl)ethyl)-2,6-methano-3-benzazocine-8-carboxamide (37). Prepared using Method A and 2-(naphthalen-2-yl)ethanamine. Off-white foam (93 mg, 55%). ¹H NMR (300 MHz, CDCl₃) δ 7.77 (m, 3H), 7.65 (s, 2H), 7.3-7.5 (m, 4H), 7.04 (d, 1H, J=7.8 Hz), 6.5 (t, 1H, J=6 Hz), 3.75 (q, 2H, J=6.4 Hz), 3.1 (m, 3H), 2.9 (d, 1H, J=19 Hz), 2.65 (m, 2H), 2.45 (dd, 1H, $J_1$=6.5 Hz, $J_2$=12.5 Hz), 2.30 (dd, 1H, $J_1$=6.6 Hz, $J_2$=12.9 Hz), 1.90 (m, 3H), 1.33 (s, 3H), 1.30 (d, 1H, J=11.1 Hz), 0.85 (m, 1H), 0.79 (d, 3H, J=7.2 Hz), 0.51 (d, 2H, J=6.6 Hz), 0.10 (m, 2H). MS (ESI) m/z 453 (M+H)+; Anal. Calcd. for $C_{31}H_{36}N_2O.1.0H_2O$: C, 79.11; H, 8.14; N, 5.95. Found: C, 79.31; H, 7.83; N, 5.92.

(±)-3-(Cyclopropylmethyl)-1,2,3,4,5,6-hexahydro-cis-6,11-dimethyl-N-(3-(naphthalen-2-yl)propyl)-2,6-methano-3-benzazocine-8-carboxamide (38). Prepared using Method A and 3-(naphthalen-2-yl)propan-1-amine. Off-white foam (85 mg, 56%). ¹H NMR (300 MHz, CDCl₃) δ 7.8 (m, 3H), 7.66 (s, 2H), 7.4-7.5 (m, 2H), 7.37 (d, 1H, J=8.3 Hz), 7.26 (m, 1H), 7.03 (d, 1H, J=7.8 Hz), 6.08 (t, 1H, J=6 Hz), 3.54 (q, 2H, J=6.5 Hz), 3.15 (m, 1H), 2.94 (d, 1H, J=20 Hz), 2.91 (t, 2H, J=7.5 Hz), 2.65 (m, 2H), 2.44 (dd, 1H, $J_1$=6.5 Hz, $J_2$=12.5 Hz), 2.31 (dd, 1H, $J_1$=6.6 Hz, $J_2$=12.9 Hz), 2.07 (m, 2H), 1.90 (m, 3H), 1.41 (s, 3H), 1.34 (m, 1H), 0.87 (m, 1H), 0.82 (d, 3H, J=7 Hz), 0.52 (m, 2H), 0.11 (m, 2H). MS (ESI) m/z 467 (M+H)+; Anal. Calcd. for $C_{32}H_{38}N_2O.0.3H_2O$: C, 81.42; H, 8.24; N, 5.93. Found: C, 81.33; H, 8.19; N, 5.89.

(±)-3-(Cyclopropylmethyl)-1,2,3,4,5,6-hexahydro-cis-6,11-dimethyl-N-(2-(naphthalen-1-yl)ethyl)-2,6-methano-3-benzazocine-8-carboxamide (40). Prepared using Method A and 2-(naphthalen-1-yl)ethanamine. Off-white foam (77.5 mg, 24%). ¹H NMR (300 MHz, CDCl₃) δ 8.19 (d, 1H, J=8.1 Hz), 7.89 (d, 1H, J=7.8 Hz), 7.78 (d, 1H, J=7.8 Hz), 7.3-7.6 (m, 6H), 7.08 (d, 1H, J=8 Hz), 6.16 (t, 1H, J=6 Hz), 3.83 (q, 2H, J=6.5 Hz), 3.44 (t, 2H, J=7 Hz), 3.19 (s, 1H), 2.95 (d, 1H, J=19 Hz), 2.7 (m, 2H), 2.49 (dd, 1H, $J_1$=6.4 Hz, $J_2$=12.7 Hz), 2.35 (dd, 1H, $J_1$=6.8 Hz, $J_2$=12.4 Hz), 1.90 (m, 3H), 1.38 (s, 3H), 1.35 (m, 1H), 0.9 (m, 1H), 0.82 (d, 3H, J=7.2 Hz), 0.53 (m, 2H), 0.13 (m, 2H). MS (ESI) m/z 453 (M+H)+; Anal. Calcd. for $C_{31}H_{36}N_2O.0.4H_2O$: C, 80.97; H, 8.07; N, 6.09. Found: C, 81.00; H, 7.98; N, 6.03.

(±)-3-(Cyclopropylmethyl)-1,2,3,4,5,6-hexahydro-cis-6,11-dimethyl-N-(3-(naphthalen-2-yl)propyl)-2,6-methano-3-benzazocine-8-carboxamide (41). Prepared using Method A and 3-(naphthalen-2-yl)propan-1-amine. White foam (60 mg, 41%). ¹H NMR (300 MHz, CDCl₃) δ 8.04 (d, 1H, J=8 Hz), 7.86 (d, 1H, J=7.3 Hz), 7.73 (d, 1H, J=7.6 Hz), 7.65 (s, 1H), 7.3 (m, 5H), 7.08 (d, 1H, J=8 Hz), 6.05 (t, 1H, J=6 Hz), 3.57 (q, 2H, J=6.8 Hz), 3.19 (t, 2H, J=7.7 Hz), 3.15 (m, 1H), 2.95 (d, 1H, J=19 Hz), 2.65 (m, 2H), 2.46 (dd, 1H, $J_1$=6.5 Hz, $J_2$=12.6 Hz), 2.31 (dd, 1H, $J_1$=6.6 Hz, $J_2$=12.4 Hz), 2.11 (m, 2H), 1.90 (m, 3H), 1.41 (s, 3H), 1.37 (d, 1H, J=11.5 Hz), 0.87 (m, 1H), 0.82 (d, 3H, J=7 Hz), 0.50 (m, 2H), 0.11 (m, 2H). MS (ESI) m/z 467 (M+H)+; Anal. Calcd. for C$_{32}$H$_{38}$N$_2$O.0.5H$_2$O: C, 80.80; H, 8.26; N, 5.89. Found: C, 80.90; H, 8.09; N, 5.87.

(−)-Q-naltrexone (71). Prepared using Scheme 2 and 2-(biphenyl-4-yl)ethanamine. White foam (160 mg, 61%). $^1$H NMR (500 MHz, CDCl$_3$) δ 7.82 (d, 1H, J=7.8 Hz), 7.73 (t, 1H, J=5.6 Hz), 7.58 (d, 2H, J=7.0 Hz), 7.54 (d, 2H, J=8.3 Hz), 7.42 (m, 4H), 7.33 (t, 1H, J=7.5 Hz), 6.81 (d, 1H, J=8.1 Hz), 5.2 (bs, 1H), 4.75 (s, 1H), 3.81 (m, 1H), 3.73 (m, 1H), 3.22 (d, 1H, J=5.9 Hz), 3.12 (d, 1H, J=19.1 Hz), 3.05 (m, 3H), 2.71 (dd, 1H, J$_1$=12.2 Hz, J$_2$=4.6 Hz), 2.63 (dd, 1H, J$_1$=9.1 Hz, J$_2$=6.0 Hz), 2.44 (dt, 1H, J$_1$=5.2 Hz, J$_2$=12.5 Hz), 2.41 (d, 2H, J=6.3 Hz), 2.32 (td, 1H, J$_1$=3.0 Hz, J$_2$=14.4 Hz), 2.08 (dt, 1H, J$_1$=3.6 Hz, J$_2$=12.2 Hz), 1.92 (m, 1H), 1.58 (dt, 1H, J$_1$=3.4 Hz, J$_2$=14.0 Hz), 1.50 (dd, 1H, J$_1$=2.5 Hz, J$_2$=12.9 Hz), 0.87 (m, 1H), 0.57 (m, 2H), 0.15 (m, 2H). MS (ESI) m/z 549 (M+H)+; Anal. Calcd. for C$_{35}$H$_{36}$N$_2$O$_4$.0.75H$_2$O: C, 74.78; H, 6.67; N, 4.89. Found: C, 74.71; H, 6.67; N, 4.95. [α]$^{25}_D$=−108.6° (c=0.75, acetone).

(−)-Q-buprenorphine (75). Prepared using Scheme 2 and 2-(biphenyl-4-yl)ethanamine. White foam (150 mg, 73%). $^1$H NMR (500 MHz, CDCl$_3$) δ 7.87 (d, 1H, J=7.8 Hz), 7.56 (d, 2H, J=7.1 Hz), 7.52 (d, 2H, J=8.0 Hz), 7.44 (t, 2H, J=7.6 Hz), 7.37 (t, 1H, J=5.6 Hz), 7.33 (t, 1H, J=7.5 Hz), 7.26 (d, 2H, J=7.8 Hz), 6.74 (d, 1H, J=8.0 Hz), 5.64 (s, 1H), 4.47 (s, 1H), 3.74 (q, 2H, J=6.6 Hz), 3.22 (s, 3H), 2.85-3.1 (m, 5H), 2.63 (dd, 1H, J$_1$=5.0 Hz, J$_2$=11.9 Hz), 2.2-2.4 (m, 4H), 2.12 (t, 1H, J=9.8 Hz), 1.97 (dt, 1H, J$_1$=5.6 Hz, J$_2$=13.0 Hz), 1.80 (t, 1H, J=12.8), 1.61 (m, 2H), 1.32 (s, 3H), 1.29 (m, 1H), 1.06 (m 1H), 1.03 (s, 9H), 0.80 (m, 1H), 0.63 (m, 1H), 0.49 (m, 2H), 0.12 (m, 2H). MS (ESI) m/z 675 (M+H)+; Anal. Calcd. for C$_{44}$H$_{54}$N$_2$O$_4$.0.25H$_2$O: C, 77.78; H, 8.09; N, 4.12. Found: C, 77.64; H, 8.03; N, 4.05. [α]$^{25}_D$=−68.3° (c=0.75, acetone).

(−)-Q-nalbuphine (77). Prepared using Scheme 2 and 2-(biphenyl-4-yl)ethanamine. White foam (170 mg, 59%). $^1$H NMR (500 MHz, CDCl$_3$) δ 7.85 (d, 1H, J=8.0 Hz), 7.57 (d, 2H, J=7.3 Hz), 7.53 (d, 2H, J=8.1 Hz), 7.54 (t, 1H, J=5.6 Hz), 7.42 (t, 2H, J=7.2 Hz), 7.33 (t, 1H, J=7.3 Hz), 7.30 (d, 2H, J=8.0 Hz), 6.75 (d, 1H, J=8.1 Hz), 4.9 (bs, 1H), 4.65 (s, 1H), 4.16 (bs, 1H), 3.81 (m, 1H), 3.63 (m, 1H), 3.12 (d, 1H, J=19.1 Hz), 3.00 (m, 1H), 2.95 (m, 1H), 2.81 (d, 1H, J=5.9 Hz), 2.65 (dd, 1H, J$_1$=19.0 Hz, J$_2$=6.3 Hz), 2.47 (m, 4H), 2.17 (m, 2H), 2.06 (m, 2H), 1.91 (m, 1H), 1.86 (m, 1H), 1.55-1.75 (m, 4H), 1.40 (m, 2H), 1.06 (m, 1H). MS (ESI) m/z 565 (M+H)+; Anal. Calcd. for C$_{36}$H$_{40}$N$_2$O$_4$.0.0H$_2$O: C, 76.57; H, 7.14; N, 4.96. Found: C, 76.54; H, 7.22; N, 4.92. [α]$^{25}_D$=−109.3° (c=0.75, acetone).

(−)-Q-butorphanol (79). Prepared using Scheme 2 and 2-(biphenyl-4-yl)ethanamine. White foam (75 mg, 81%). $^1$H NMR (500 MHz, CDCl$_3$) δ 7.69 (S, 1H), 7.57 (d, 2H, J=7.0 Hz), 7.54 (d, 2H, J=8.0 Hz), 7.44 (d, 1H, J=7.3 Hz), 7.43 (t, 2H, J=7.8 Hz), 7.33 (t, 1H, J=7.3 Hz), 7.30 (d, 2H, J=8.0 Hz), 7.11 (d, 1H, J=7.8 Hz), 6.4 (bs, 1H), 4.6 (bs, 1H), 3.72 (m, 2H), 3.10 (d, 1H, J=18.8 Hz), 2.96 (t, 2H, J=7.1 Hz), 2.81 (dd, 1H, J$_1$=6.2 Hz, J$_2$=19 Hz), 2.64 (d, 1H, J=6.1 Hz), 2.45 (m, 3H), 2.34 (m, 1H), 1.75-2.10 (m, 9H), 1.65 (m, 2H), 1.50 (m, 1H), 1.2-1.45 (m, 4H), 0.97 (m, 1H). MS (ESI) m/z 535 (M+H)+; Anal. Calcd. for C$_{36}$H$_{42}$N$_2$O$_2$0.33H$_2$O: C, 79.97; H, 7.95; N, 5.18. Found: C, 79.92; H, 8.03; N, 5.19. [α]$^{25}_D$=−54.8° (c=0.75, acetone).

Q-naltrexone ring opened (81.). Prepared using the method described in published US application 2006/0111384, which derives from Coop et al., "δ Opioid Affinity and Selectivity of 4-Hydroxy-3-methoxyindolomorphianan Analogues Related to Naltrindole", *J. Med. Chem.* 1999, 42, 1673. Zinc dust (65 mg, 3.75 mmol) was added in portions over 20 min to a solution of (−)-71 Q-naltrexone (103 mg, 0.19 mmol), in HCl (37%, 0.2 mL) and AcOH (5 mL) at reflux. After heating at reflux for a further 10 min, the reaction was cooled by the addition of ice/water (50 mL) and basified (pH 9) with NH$_4$OH, and the products were extracted into CH$_2$Cl$_2$ (3×50 mL). The organic extracts were washed with brine (100 mL), dried, concentrated, and purified by column chromatography (SiO$_2$, CH$_2$Cl$_2$:CH$_3$OH:NH$_4$OH 25:1:0.1) to give 81 (71.7 mg, 70%): $^1$H NMR (300 MHz, CDCl$_3$) δ 13.33 (s, 1H), 7.59 (d, 2H, J=7.8 Hz), 7.57 (d, 2H, J=8.1 Hz), 7.45 (t, 2H, J=7.4 Hz), 7.36 (t, 1H, J=7.5 Hz), 7.32 (d, 2H. J=8.1 Hz), 6.93 (d, 1H, J=8.1 Hz), 6.44 (d, 1H, J=8.4 Hz), 6.38 (bt, 1H), 4.70 (bs, 1H), 4.10 (d, 1H, J=13.5 Hz), 3.70 (m, 2H), 3.11 (d, 1H, J=6.0 Hz), 2.9-3.0 (m, 4H), 2.76-2.87 (m, 2H), 2.63 (m, 1H), 2.35 (d, 2H, J=6.5 Hz), 1.5-2.2 (m, 8H), 0.87 (m, 1H), 0.59 (m, 2H), 0.11 (m, 2H). MS (ESI) m/z 551 (M+H)+; Anal. Calcd. for C$_{35}$H$_{38}$N$_2$O$_4$.0.3H$_2$O: C, 75.60; H, 7.00; N, 5.04. Found: C, 75.56; H, 6.90; N, 4.87.

In general, the chemistry described above works in the presence of the variety of functional groups found on known core structures. The exceptions would be morphine and congeners having a free 6-OH, which can be protected by a TBDPS (t-butyldiphenylsilyl) group [see Wentland et al., "Selective Protection and Functionalization of Morphine . . . ", *J. Med. Chem.* 43, 3558-3565 (2000)].

I claim:
1. A compound of formula:

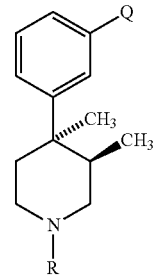

wherein R is —CH$_3$, —CH$_2$CH$_2$CH(OH)C$_6$H$_{11}$, —CH$_2$CH(CH$_2$Ph)CONHCH$_2$CO$_2$H, —(CH—$_2$)$_3$CH(CH$_3$)$_2$ or —(CH$_2$)$_3$-2-thienyl;
wherein Q is

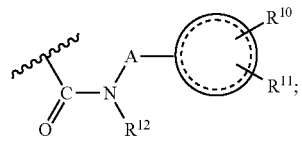

wherein

is an aryl or heteroaryl residue of one to three rings;
A is (CH$_2$)n, wherein one or more CH$_2$ may be replaced by —O—, cycloalkyl or CR$^{1a}$R$^{1b}$;
R$^{1a}$ and R$^{1b}$ are chosen independently from hydrogen, halogen, lower alkyl, lower alkoxy and lower alkylthio;

$R^{10}$ is one or two residues chosen independently from hydrogen, hydroxyl, halogen, $(C_1-C_6)$alkyl, $(C_1-C_6)$alkoxy, halo$(C_1-C_6)$alkyl and halo$(C_1-C_6)$alkoxy and $(C_1-C_6)$alkylthio;

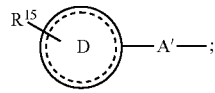

$R^{11}$ is H or

is an aryl or heteroaryl residue of one to three rings;
A' is $(CH_2)_m$ wherein one or more $CH_2$ may be replaced by —O—, cycloalkyl, —$CR^{1a}R^{1b}$, —C(=O)— or —NH—;
$R^{12}$ is chosen from hydrogen and lower alkyl;
$R^{15}$ is one or two residues chosen independently from hydrogen, hydroxyl, halogen, $(C_1-C_6)$alkyl, $(C_1-C_6)$alkoxy, halo$(C_1-C_6)$alkyl and halo$(C_1-C_6)$alkoxy and $(C_1-C_6)$alkylthio;
m is zero or an integer from 1 to 6; and
n is an integer from 1 to 6;
with the proviso that A is other than $CH_2$.

* * * * *